US011801038B2

(12) United States Patent
Nielsen et al.

(10) Patent No.: US 11,801,038 B2
(45) Date of Patent: Oct. 31, 2023

(54) ULTRASOUND IMAGING SYSTEM TOUCH PANEL WITH MULTIPLE DIFFERENT CLUSTERS OF CONTROLS

(71) Applicant: B-K Medical Aps, Herlev (DK)

(72) Inventors: Torben Svanberg Nielsen, Copenhagen (DK); John Antol, Nahant, MA (US); Kaj Dunkin, Stenlille (DK); Jesper Helleso Hansen, Copenhagen (DK)

(73) Assignee: BK Medical APS, Herlev (DK)

( * ) Notice: Subject to any disclaimer, the term of this patent is extended or adjusted under 35 U.S.C. 154(b) by 1586 days.

(21) Appl. No.: 15/529,621

(22) PCT Filed: Nov. 26, 2014

(86) PCT No.: PCT/IB2014/066363
§ 371 (c)(1),
(2) Date: May 25, 2017

(87) PCT Pub. No.: WO2016/083868
PCT Pub. Date: Jun. 2, 2016

(65) Prior Publication Data
US 2017/0258449 A1      Sep. 14, 2017

(51) Int. Cl.
*A61B 8/00* (2006.01)
*A61B 6/00* (2006.01)
(Continued)

(52) U.S. Cl.
CPC .............. *A61B 8/465* (2013.01); *A61B 5/055* (2013.01); *A61B 5/7435* (2013.01);
(Continued)

(58) Field of Classification Search
None
See application file for complete search history.

(56) References Cited

U.S. PATENT DOCUMENTS

| 6,063,030 A | * | 5/2000 | Vara | ........................ | G16H 40/63 |
| | | | | | 600/437 |
| 6,436,040 B1 | * | 8/2002 | Collamore | ............... | A61B 8/02 |
| | | | | | 600/437 |

(Continued)

FOREIGN PATENT DOCUMENTS

| FR | 2861192 A1 | 4/2005 |
| JP | 2006020668 A | 1/2006 |
| JP | 2010142399 A | 7/2010 |

OTHER PUBLICATIONS

International Search Report for PCT/IB2014/066363, published as WO2016083868 dated Jun. 2, 2016.

*Primary Examiner* — Angela M Hoffa
*Assistant Examiner* — Younhee Choi
(74) *Attorney, Agent, or Firm* — Dugherty & Del Zoppo, Co. LPA

(57) ABSTRACT

An ultrasound imaging system (102) includes a touch screen user interface (122) and a touch screen controller (148). The touch screen user interface includes a touch panel (124). The touch panel includes a plurality of different clusters (510-522) of controls including a first cluster (512) in first sub-region and with a tactile control and one or more other cluster (510 and 514-522) in one or more other different sub-regions and with soft controls. The touch screen controller visually renders the one or more other clusters in the one or more different sub-regions spatially arranged with respect to each other based on a predetermined control cluster configuration for the touch screen user interface. The one or more other clusters include controls that correspond to different groupings of ultrasound imaging operations of the ultrasound imaging system.

47 Claims, 16 Drawing Sheets

(51) Int. Cl.
*A61B 5/055* (2006.01)
*A61B 5/00* (2006.01)
*G06F 3/04845* (2022.01)
*G06F 3/04847* (2022.01)
*G06F 3/04886* (2022.01)
*A61B 8/08* (2006.01)

(52) U.S. Cl.
CPC ............ *A61B 5/7475* (2013.01); *A61B 6/465* (2013.01); *A61B 6/468* (2013.01); *A61B 6/54* (2013.01); *A61B 8/463* (2013.01); *A61B 8/467* (2013.01); *A61B 8/468* (2013.01); *A61B 8/483* (2013.01); *A61B 8/486* (2013.01); *A61B 8/488* (2013.01); *A61B 8/54* (2013.01); *G06F 3/04845* (2013.01); *G06F 3/04847* (2013.01); *G06F 3/04886* (2013.01); *A61B 5/7455* (2013.01)

(56) References Cited

U.S. PATENT DOCUMENTS

| | | | |
|---|---|---|---|
| 9,119,586 B2* | 9/2015 | Jensen | A61B 8/461 |
| 9,414,810 B2* | 8/2016 | Dunkan | A61B 8/4438 |
| 2003/0013959 A1* | 1/2003 | Grunwald | A61B 8/08 |
| | | | 600/437 |
| 2008/0200868 A1* | 8/2008 | Alberti | A61M 1/28 |
| | | | 604/29 |
| 2009/0227872 A1* | 9/2009 | Pan | A61B 8/481 |
| | | | 600/458 |
| 2010/0002135 A1* | 1/2010 | Dodd | H04N 21/42204 |
| | | | 348/553 |
| 2010/0090877 A1* | 4/2010 | Dunbar | A61B 8/467 |
| | | | 341/176 |
| 2010/0217128 A1* | 8/2010 | Betts | A61B 8/14 |
| | | | 600/459 |
| 2011/0184824 A1* | 7/2011 | George | G06Q 20/209 |
| | | | 705/25 |
| 2014/0282142 A1* | 9/2014 | Lin | A61B 8/467 |
| | | | 715/765 |
| 2015/0182196 A1* | 7/2015 | Ninomiya | A61B 8/467 |
| | | | 600/437 |

* cited by examiner

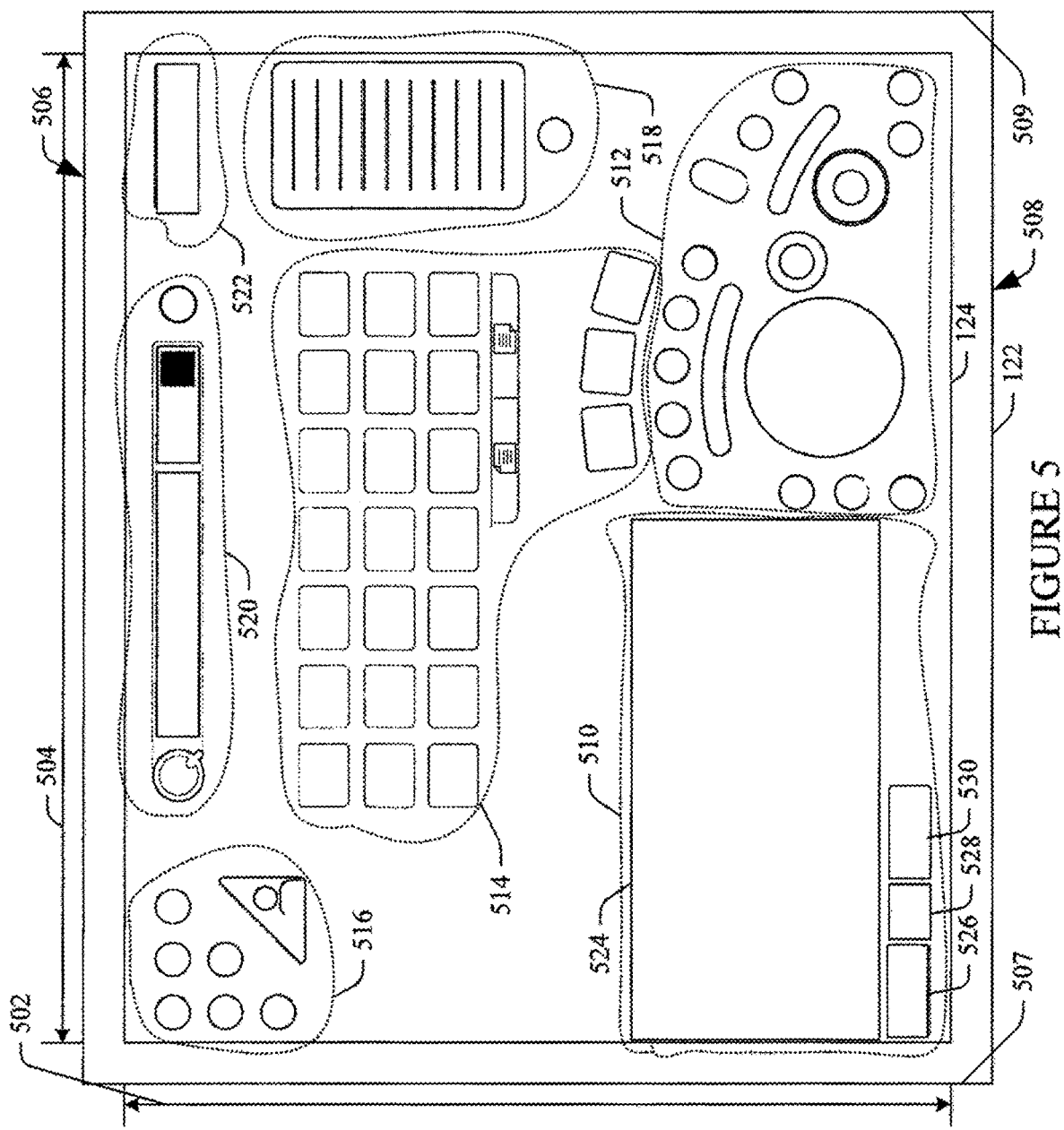

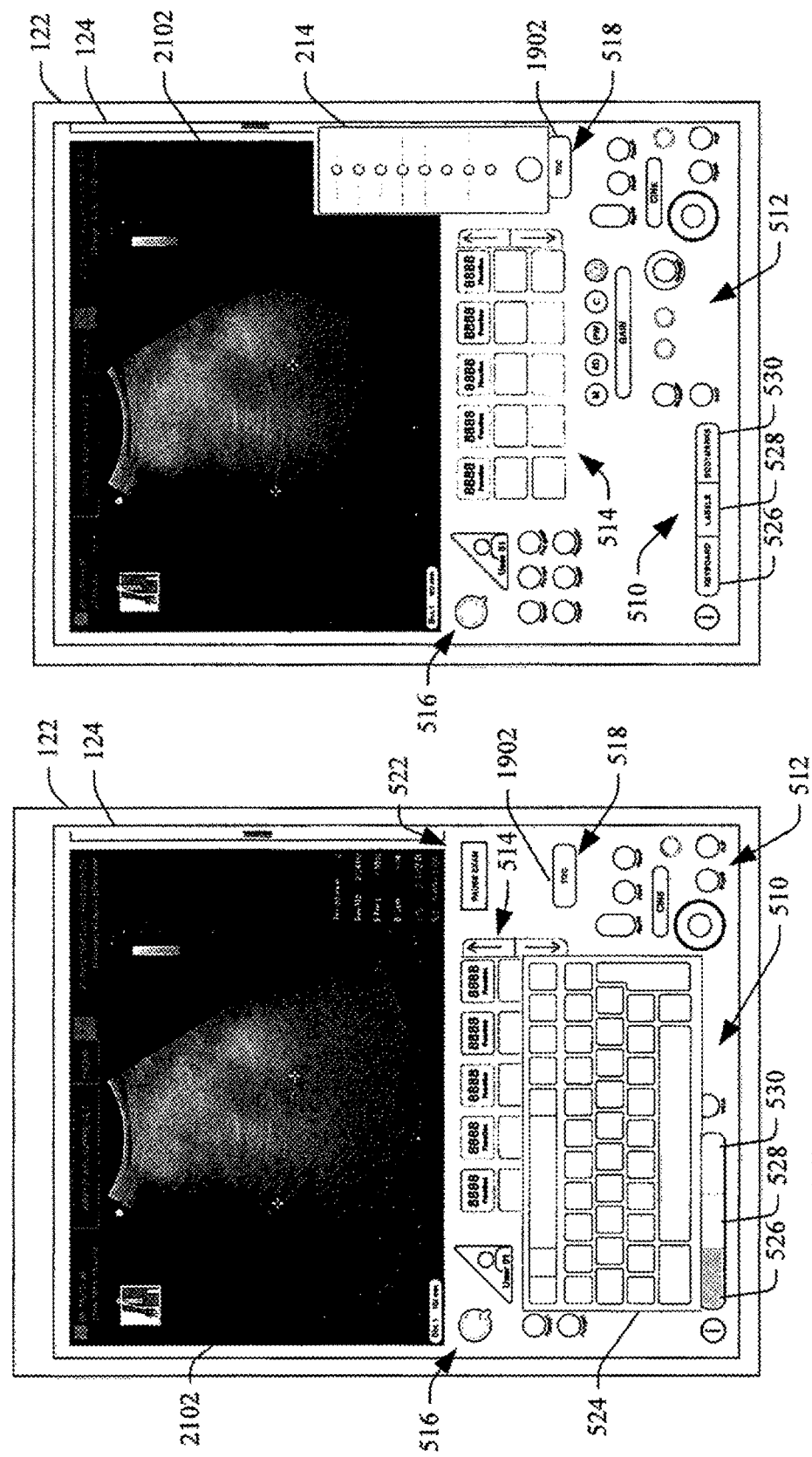

ULTRASOUND IMAGING SYSTEM TOUCH PANEL WITH MULTIPLE DIFFERENT CLUSTERS OF CONTROLS

RELATED APPLICATION

This application is a national filing of PCT application Serial No. PCT/IB2014/066363, filed Nov. 26, 2014, published as WO2016/083868 on Jun. 2, 2016. This application claims priority to PCT application Serial No. PCT/IB2014/066363, published as WO2016/083868 on Jun. 2, 2016.

TECHNICAL FIELD

The following generally relates to ultrasound imaging and more particular to a touch panel of an ultrasound imaging system with multiple different clusters of controls.

BACKGROUND

An ultrasound imaging system has included an ultrasound probe with a transducer, a console with an integrated or external display monitor, and a user interface. The transducer transmits an ultrasound signal into a field of view and receives echoes produced in response to the signal interacting with structure therein. The echoes are conveyed to the console and are processed, producing images of the scanned structure, which may be visually presented through the display monitor.

The display monitor may include a cathode ray tube (CRT), a liquid crystal display (LCD), a light emitting diode (LED) display, and/or other type of display. The display monitor has been a "dumb" monitor with no processor or processing capabilities and that is simply an output device that displays images and other information (e.g., transducer frequency, gain, etc.). The user interface has included a keyboard or keypad with mechanical depressible buttons and/or a flat touch screen area (e.g., LCD, CRT, etc.).

The display monitor has been placed in an upright vertical position so that the clinician can look at images and/or the other information displayed via the display monitor. The user interface has been placed in a generally horizontal position, approximately perpendicular to the upright vertical position. This arrangement is similar to that of a desktop computer monitor and corresponding keyboard. The user controls features such as gain, zoom, pans, etc. with the controls of the user interface.

Unfortunately, with such a user interface/display monitor arrangement, where the user interface includes a touch screen with a flat surface, it may not be readily easy for the user to locate and/or operate touch sensitive controls of the user interface while observing an image and/or patient. Rather, the user may have to look away from the image and/or patient and down at the user interface to find and/or operate the control, adding complexity and inefficiency to the procedure.

SUMMARY

Aspects of the application address the above matters, and others.

In one aspect, an ultrasound imaging system includes a touch screen user interface and a touch screen controller. The touch screen user interface includes a touch panel. The touch panel includes a plurality of different clusters of controls including a first cluster in first sub-region and with a tactile control and one or more other cluster in one or more other different sub-regions and with soft controls. The touch screen controller visually renders the one or more other clusters in the one or more different sub-regions spatially arranged with respect to each other based on a predetermined control cluster configuration for the touch screen user interface. The one or more other clusters include controls that correspond to different groupings of ultrasound imaging operations of the ultrasound imaging system.

In another aspect, a method includes obtaining, by a controller, a control cluster configuration for a touch panel of a touch screen user interface from of an ultrasound imaging system from a memory device of the ultrasound imaging system. The control cluster configuration identifies a plurality of different clusters of controls. The method further includes constructing, with the controller, a display for the touch panel of the touch screen user interface based on the plurality of different clusters of controls. The method further includes visually rendering, with the controller, the constructed display on the touch panel of the touch screen user interface. The method further includes performing an ultrasound imaging function in response to receiving a signal from an activated one of the visually rendered controls of the plurality of different clusters of controls.

In another aspect, a touch screen user interface includes a touch panel configured to display a plurality of clusters of controls, wherein each cluster of the plurality of clusters is displayed in a predetermined region of the touch panel, wherein at least one of the clusters is a primary cluster with a tactile control stationarily positioned at a fixed, non-moveable location proximate to a user, and wherein the other clusters include a variable set of soft controls.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 5 illustrates an example of the touch screen user interface with multiple clusters of controls;

FIG. 6 illustrates an example ultrasound imaging system with the touch screen user interface of FIG. 5;

FIG. 25 illustrate the variation of FIG. 24 in connection with the annotation cluster;

FIG. 26 illustrate the variation of FIG. 24 in connection with the TGC cluster;

DETAILED DESCRIPTION

Figure 1:
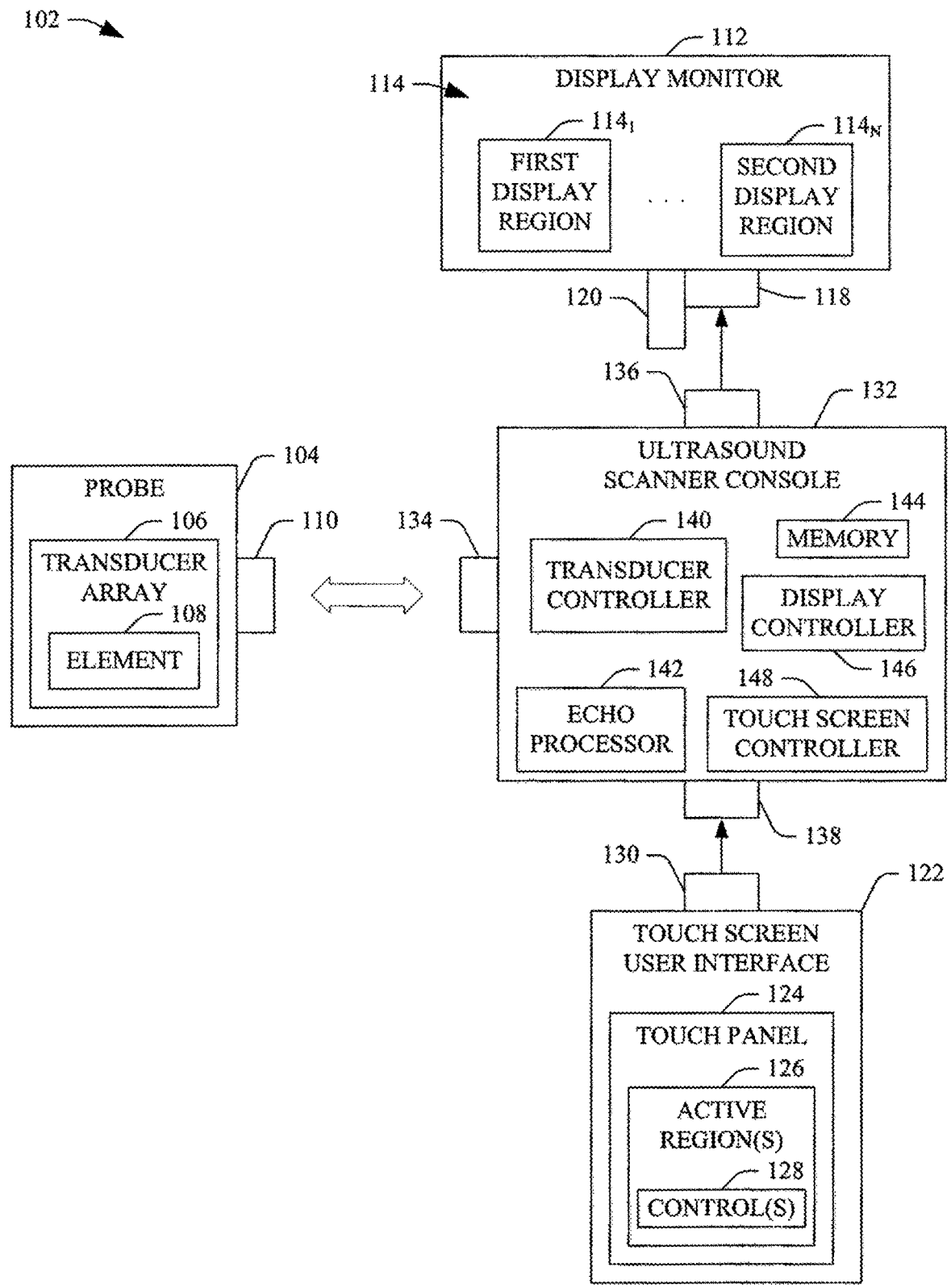
FIG. 1 schematically illustrates an example ultrasound imaging system with a touch screen user interface.

FIG. 1 schematically illustrates an ultrasound (US) imaging system 102.

The ultrasound imaging system 102 includes a probe 104 with a one-dimensional (1D) or two-dimensional (2D) transducer array 106 with at least one transducer element 108. Suitable array configurations include, but are not limited to, linear, curved (e.g., concave, convex, etc.), circular, etc., full populated or sparse, etc. The probe 104 further includes a console interface 110, which may include a connector (e.g., an electro-mechanical device for joining electrical circuits) and/or wireless transceiver.

The ultrasound imaging system 102 further includes a display monitor 112. The display monitor 112 can be a cathode ray tube (CRT), a liquid crystal display (LCD), a light emitting diode (LED), and/or other display monitor. The display monitor 112 includes a display area 114 with a multiple sub-display regions $114_1, \ldots, 114_N$, where N is a positive integer. The display monitor 112 further includes a console interface 110, which may include a connector (e.g., an electro-mechanical device for joining electrical circuits) and/or wireless receiver.

The display monitor 112 can be affixed to a support 120 (as shown in FIG. 1) such as a stand, a bracket, etc. that rests on or is affixed to a surface (e.g., a desk, a table, etc.) and holds the display monitor 112 in a generally upright vertical viewing position. In another instance, the support 120 can be a wall bracket that mounts to a wall, a ceiling, etc., thereby indirectly mounting the display monitor 112 thereto. Other supports are also contemplated herein. The support 120 may be configured to rotate, tilt, translate, and/or otherwise move, which selectively allows for spatially orienting the region 114.

The ultrasound imaging system 102 further includes a touch screen user interface 122. The touch screen user interface 122 includes a touch panel 124. At least a sub-portion of the touch panel 124 includes one or more active regions 126 with one or more touch sensitive control(s) 128 such as a time-gain control (TGC), a mode (e.g., 2D, 3D, 4D, pulse wave (PW) Doppler, Color (Col) Doppler, M, etc.) selector control, a CINE control, a measurement control, an ultrasound imaging parameter control (e.g., zoom, a depth, focus, etc.), etc. The touch panel 124 may include a resistive, a capacitive, an acoustic, an infrared, an optical, a piezoelectric, and/or other region. Furthermore, the touch panel 124 may include an LCD, thin film transistor (TFT) LCD, organic light-emitting diode (OLED), and/or other display.

The one or more controls 128, in one instance, are kept in a normally de-activated state, but can be activated. A de-activated control 128, when actuated by a gesture (e.g., a press, a swipe, a touch, etc.) on the control 128 with one or more fingers, a stylus, a glove, etc., transitions to an active state. An activate control 128, when operated, generates an electrical signal corresponding to the operation of the control 128. Generally, when a control 128 is active, one or more other non-active controls transition to a non-activated state. In a variation, one or more controls can be kept in a normally active state. In this variation, the normally active control may transition to a de-active state in response to activation of another control, a gesture over the control, an input signal including a control signal that de-activates the control, etc.

As an example of activation and operation, a gain control is activated by touching the control and then the gain is increased or decreased (i.e., operated) through the control through a predetermined gesture. For example, circling clockwise, sliding over in direction, etc. the gain control with a suitable object increases gain, and circling counter-clockwise, sliding in another direction, etc. over the gain control with the suitable object decreases gain. A reset control may be provided to quickly return on or more of the touch controls 128 to the initial or starting conditions. An active control can be configured to automatically transition back to a de-active state, e.g., in response to lapse of a predetermined length of time of inactivity, activation of another control 128, on demand, etc.

Figure 2:
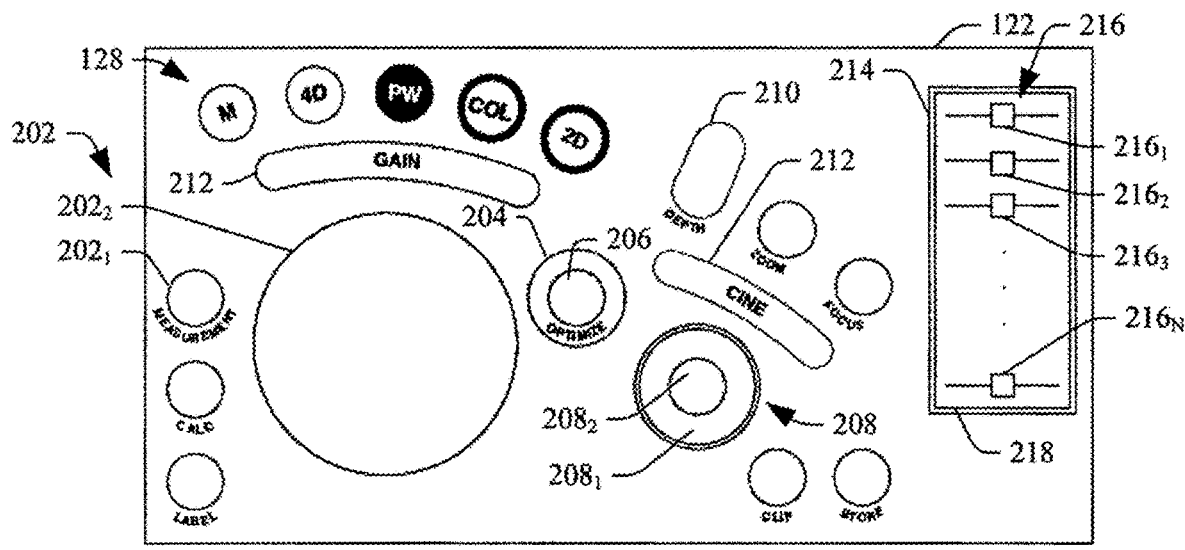
FIG. 2 illustrates an example of a cluster of controls for the touch screen user interface.
Figure 3:
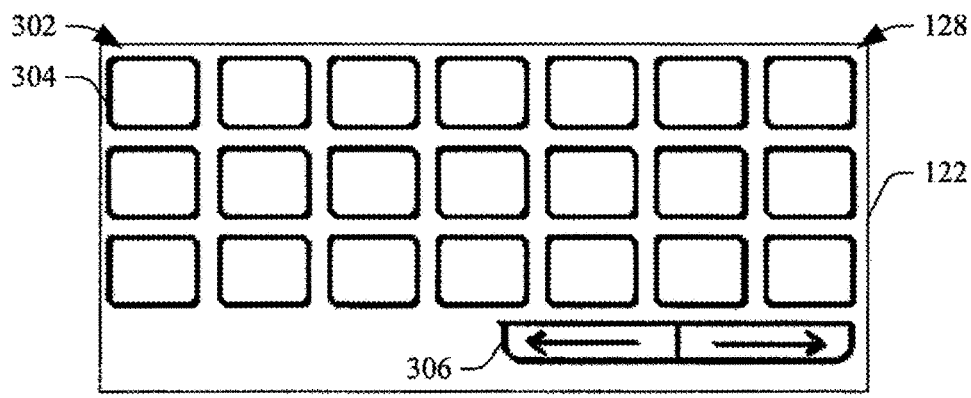
FIG. 3 illustrates another example of a cluster of controls for the touch screen user interface.
Figure 4:
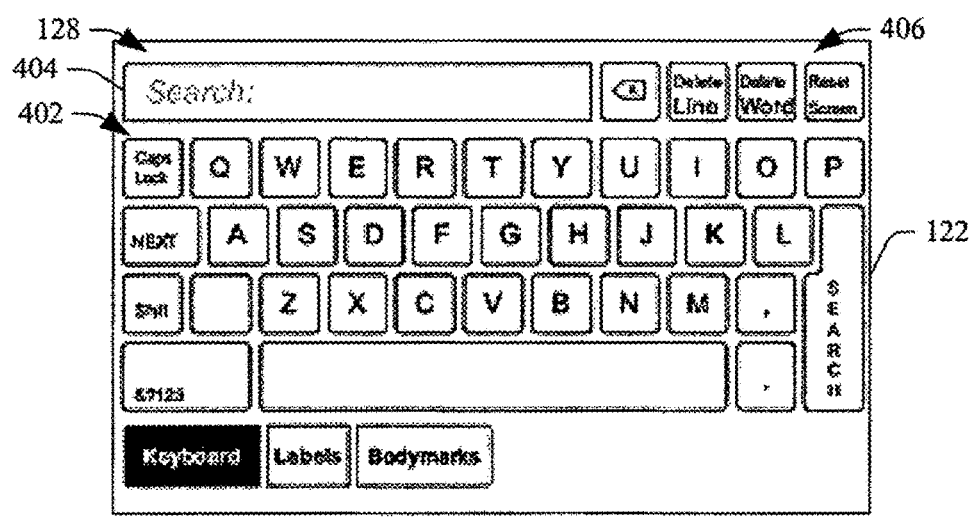
FIG. 4 illustrates another example of a cluster of controls for the touch screen user interface.

Briefly turning to FIGS. 2, 3 and 4, non-limiting examples of the touch screen user interface 122 are illustrated.

In FIG. 2, the controls 128 include circular shaped controls 202 including one control $202_1$ with one diameter and another control $202_2$ with a different larger diameter, a ring shape control 204 with a non-active area 206 in the hole of the ring, concentric controls 208 including one control $208_1$ surrounded by another control $208_1$, a rectangular control 210 with rounded edges, and curved rectangular controls 212 with rounded edges. A control 214 includes a plurality of touch activated slides $216_1, 216_2, 216_3, \ldots, 216_N$, collectively referred to herein as virtual slides 216, which reside in a recess 218 in the touch panel 124. Again, the controls 128 can be activated and used by pressing, tapping, swiping, etc.

Turning to FIG. 3, the controls 128 include a two-dimensional (2D) array 302 of rectangular controls 304 and other controls 306. In FIG. 4, the controls 128 include controls 402 of a computer keyboard as well as other controls 128, such as a search box 404, and custom configure controls 406. Another example touch screen user interface 122 includes a combination of FIGS. 2, 3 and/or 4, optionally with alternative and/or additional controls. Still other controls can also include physical mechanical controls such as a trackball, a track pad, etc. Other examples of touch screen controls are described in application Ser. No. 13/748,653, filed on Jan. 24, 2013, entitled "Ultrasound Imaging System," and assigned to B-K Medical Aps, which is incorporated herein by reference in its entirety.

Returning to FIG. 1, the touch screen user interface 122 may also include visual indicators (e.g., lights, etc.), audible indicators (e.g., speakers, etc.), tactile indicators (e.g., a structural surface feature such as a rough surface, a recess, an indentation, etc.), other controls (e.g., physical mechanical buttons, physical mechanical slides, physical mechanical rotary knobs, etc.), an image display region, etc. The touch screen user interface 122 further includes a console interface 130, which may include a connector (e.g., an electromechanical device for joining electrical circuits) and/or wireless transceiver.

The ultrasound imaging system 102 further includes an ultrasound scanner console 132. The console 132 includes a probe interface 134, a display monitor interface 136, and a touch screen user interface 138, which, respectively are complementary to the console interfaces 110, 118 and 130. For example, the probe interface 134 is complementary to the console interface 110 in that the probe interface 134 and the console interface 110 physically engage and provide an electrical pathway between the probe 104 and the ultrasound scanner console 132. For instance, the console interface 110 may include a female connector and the probe interface 134 may include a male connector, wherein the connectors physically engage and physically connect electrodes.

The ultrasound scanner console 132 further includes a transducer controller 140. The transducer controller 140 controls excitation of the at least one transducer element 108. The transducer controller 140 also controls detection of echoes with the at least one transducer element 108. In a variation, the excitation and detection can be through separate components such as transmit and receive circuitry. The console 132 further includes an echo processor 142 (e.g., microprocessor, central processing unit, etc.) that processes detected echoes. Such processing may include generating an image, estimating flow velocity, and/or processing. The ultrasound scanner console 132 further includes a physical memory device (memory) 144, which can be used to store ultrasound data.

A controller 146 controls the information visually presented in at least one of the display regions 114 of the display monitor 112. By way of example, in one non-limiting instance, the display controller 146 renders an ultrasound image in at least one of the display regions 114. In another example, the display controller 146 renders a graphical representation of one of the controls 128 in at least one of the display regions 114. As described in greater detail below, for the latter, the display controller 146 identifies activation and/or operation of a touch control 128 and renders the graphical representation in the at least one of the display regions 114, where the graphical representation may include alpha-numeric information and/or graphics, shows a current value and/or any changes thereto, shows movement of the actual control, etc.

Generally, the graphical representation provides a virtual control of a touch control 128, on the display monitor 112, that mirrors or mimics the touch control 128 of the touch screen user interface 122 and operation of the touch control 128 through the touch screen user interface 122. The graphical representation shows in the display monitor 112, for example, where the user's finger (or other object) is located on the touch screen user interface 122 with respect to the control 128, thereby allowing the user to adjust a control 128 without looking at the control 128 on the touch screen user interface 122. In one instance, this provides a more intuitive adaptation of the touch controls, and may reduce complexity and inefficiency, relative to a configuration in which the display controller 146 does not render virtual controls on a display region of the display monitor 112.

The ultrasound scanner console 132 further includes a touch screen controller 148. The touch screen controller 148 controls display of the controls 128 in the active region 126. In one instance, this includes obtaining a control cluster configuration for the touch screen user interface 122 from the memory 144 and/or other memory, constructing a display with clusters of controls for the touch screen user interface based on the control cluster configuration, and visually rendering the constructed display on the touch panel 124 of the touch screen user interface 122. The rendered controls 128 operate as discussed herein, for example, in connection with at least the description of FIGS. 2, 3 and 4, and/or otherwise. For example, certain controls are rendered active while other controls are rendered inactive, depending on a current mode of operation, a current step in a sequence of steps, etc.

As discussed in connection with FIGS. 2-4, another example touch screen user interface 122 includes a combination of FIGS. 2, 3 and/or 4, optionally with alternative and/or additional controls. In such instances, different groupings of controls can be considered different clusters of controls, for example, a cluster of controls corresponding to FIG. 2, a different cluster of controls corresponding to FIG. 3, another different cluster of controls corresponding to FIG. 4, and/or one or more other different clusters corresponding to one or more other controls. The spatial arrangement of the different clusters with respect to each other and/or within the touch panel 124 can be based on a default configuration, an orientation (e.g., portrait or landscape) of the touch panel 124, a size (e.g., 19" or 15") of the touch panel 124, an active mode of operation, an active control, an expected location of the user of the touch panel 124, etc.

FIGS. 5-28 illustrate non-limiting examples. Initially referring to FIGS. 5 and 6, the touch panel 124 has a width 502 and a length 504. In this example, the length 504 is greater than the width 502. As such, the illustrated configuration represents a "landscape" display configuration. A size of the touch panel 124, in one instance, has a diagonal in a range of 17" to 25", such as 19", 19.5" and/or other size. A back side 506 of the touch screen user interface 122 is proximate to the display monitor 112 and a front side 508, which opposes the back side 506, is distal to the display monitor 112. Left and right sides 507 and 509 extend between the back and front sides 506 and 508. Generally, the front side 508 of the touch screen user interface 122 is the side of the imaging system 102 that a user operating the imaging system 102, via the touch panel 124, is located.

In FIG. 6, the display monitor 112, the touch screen user interface 122 and the ultrasound scanner console 132 are integrated and part of a mobile cart 600, which include movers 602 such as wheels, casters, etc. In another configuration, the ultrasound imaging system 102 rests on a table, desk, etc., and does not include movers and is not integrated into a cart, is also contemplated herein. Returning to FIG. 5, in another example, the width 502 is greater than the length 504. Such a configuration represents a "portrait" display configuration. In another example, the width 502 and the length 504 are equal. With continuing reference to FIG. 5, the illustrated touch panel 124 includes an annotation cluster 510, a primary cluster 512, a contextual cluster 514, a pre/post cluster 516, a TGC cluster 518, an application cluster 520, and an exam cluster 522.

The primary cluster 512, which is preferably located at a fixed location on the touch screen, includes one or controls that provide the user with a tactile indication of the location of the control, for example by the way of recesses, ridges, a different surface smoothness or roughness, or the like. The tactile indication, can be provided using one or more of the methods described in application Ser. No. 13/748,653, filed on Jan. 24, 2013, entitled "Ultrasound Imaging System," which is incorporated herein by reference in its entirety. In an alternative embodiment, the tactile indication can be provided through haptic or other feedback, either alone or in combination with the techniques described above, when the user's hand or finger is placed in the vicinity of a particular control.

One or more soft non-fixed controls may also be in the primary cluster 512. In the illustrated example, the primary cluster 512 is located proximate the front side 508 of the touch screen user interface 122, distal to the back side 506. In this location, for instance, the primary cluster 512 can be readily accessed by an operator located in front of the ultrasound imaging system 102. As described herein, in one instance, the primary cluster 512 controls operations such as a mode (e.g., 2D, 3D, color Doppler, pulse wave Doppler, 4D mode, motion mode, etc.), ultrasound imaging parameter (e.g., depth, gain, zoom, focus, etc.) etc., which may be considered as primary controls. If desired, the operator can employ the recessed controls using only tactile (and/or auditory) feedback while visually observing the image displayed on the monitor 112, the subject being scanned, the ultrasound probe 104, and/or other object other than the primary cluster 512. Of course, the operator may also utilize visual feedback through visually observing the primary cluster 512.

In one embodiment, the user may operate the system by using one hand to position the transducer in relation to the patient and the other hand to operate the primary controls, while maintaining primary visual focus on the ultrasound image information on the main display. Note that, while the primary cluster 512 is shown in position proximate the user near the right hand side of the touch screen user interface 122, the primary cluster may be located in other positions, such as near to the left hand side or in a relatively central location.

The annotation cluster 510, the contextual cluster 514, the pre/post cluster 516, the TGC cluster 518, the application cluster 520, and the exam cluster 522 include soft controls, which are rendered on the touch panel 124. The location, size, number, functions controlled by, etc. of the controls and the clusters is variable in that these characteristics, as well as other characteristics, are configurable and/or changeable. In one instance, these characteristics are based on a default setting. In another instance, these characteristics are based on facility, user, etc. preferences. In one example, soft controls of a cluster such those in the annotation cluster 510, which are utilized more than other soft controls during an examination, for example, to enter alphanumerical data (e.g., via a soft keyboard), identify anatomy, identify anatomical orientation, identify probe location, etc. during an examination are rendered proximate the front side 508 of the touch screen user interface 122, distal to the back side 506. In the illustrated example, the annotation cluster 510 is located next to the primary cluster 512. Likewise, in this location, the controls of the annotation cluster 510 are readily accessible to the user.

Clusters such as the pre/post cluster 516, the application cluster 520, the exam cluster 522, etc., which include soft controls that generally are utilized less often than the controls of the other cluster during an examination, are rendered proximate the back side 506, relative to the front side 508, of the touch screen user interface 122. Rendering these clusters as such, for instance, places these controls "out of the way" of the primary cluster 512, the annotation cluster 510, etc., so that these controls do not visibly obscure and/or otherwise hinder access to the controls of the primary cluster 512, the annotation cluster 510, etc. This may further access by the operator of the ultrasound imaging system 102 to the controls of the primary cluster 512, the annotation cluster 510, etc. In another instance, the annotation cluster 510 may be rendered proximate to the back side 506 and one or more of the pre/post cluster 516, the application cluster 520, the exam cluster 522, etc. clusters are rendered proximate to the front side 508. The particular layout may depend on the setting and/or preference, and/or a currently activated control and/or mode of operation.

The primary cluster 512 includes controls for acquisition, image modes, calculations/measurement, optimization, and navigation. The contextual cluster 514 includes a dynamic area that presents functionality related to the active and in-focus image type. The pre/post cluster 516 includes controls for functionality that is accessed before and/or after an imaging examination. The TGC cluster 518 includes TGC controls. An example of TGC controls is described in international application serial number PCT/IB2014/059836, filed on Mar. 14, 2014, and entitled "GRAPHICAL VIRTUAL CONTROLS OF AN ULTRASOUND IMAGING SYSTEM, which is incorporated herein by reference in its entirety. The application cluster 520 includes controls for functionality to access the applications/presets, transducers, as well as, quick start and information. The exam cluster 522 includes controls that start, pause, resume, and/or add to exams.

The annotation cluster 510 provides controls for adding descriptors to an image visually displayed by the display monitor 112 and/or other display device. The annotation cluster 510 includes multiple different control layouts, which are alternatively visually displayed in a display region 524, for example, based on a default setting, a user selection, etc. By way of non-limiting example, the illustrated annotation cluster 510 includes multiple different control layouts, which are individually selectable via touch screen controls 526, 528 and 530. In one example, the multiple different control layouts include a keyboard, a predefined labels layout, and a bodymarker layout. In another example, more or less, including different and/or similar, control layouts are also contemplated herein.

Figure 7:
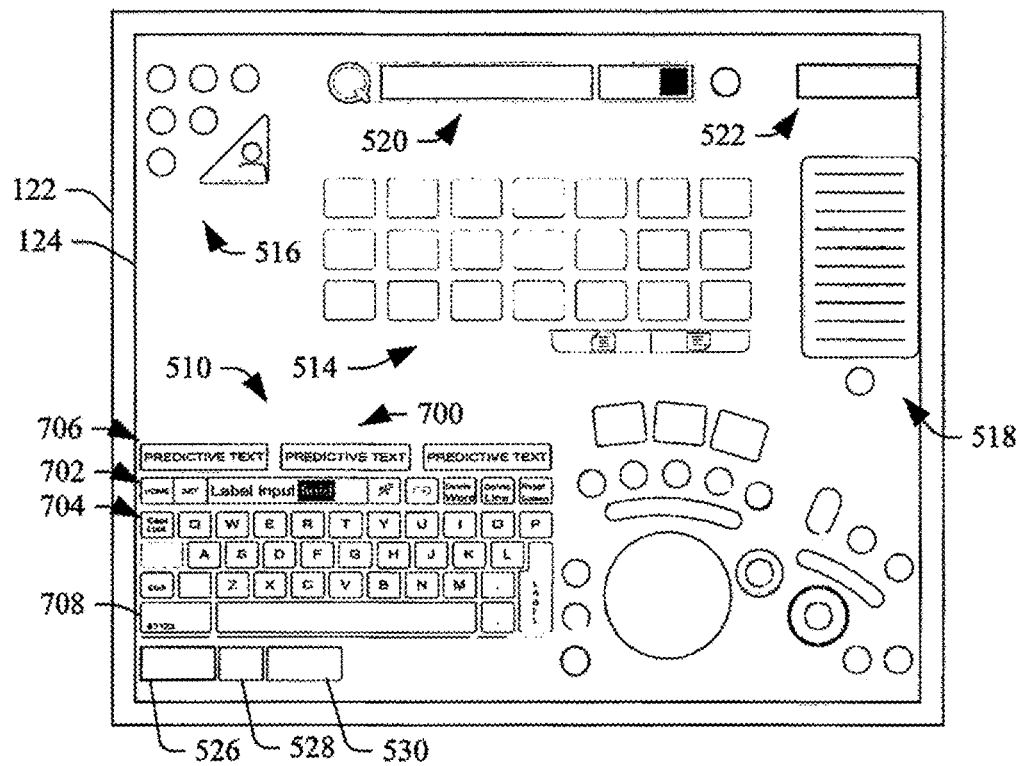
FIG. 7 illustrates an example of an annotation cluster of the touch screen user interface of FIG. 5.
Figure 8:
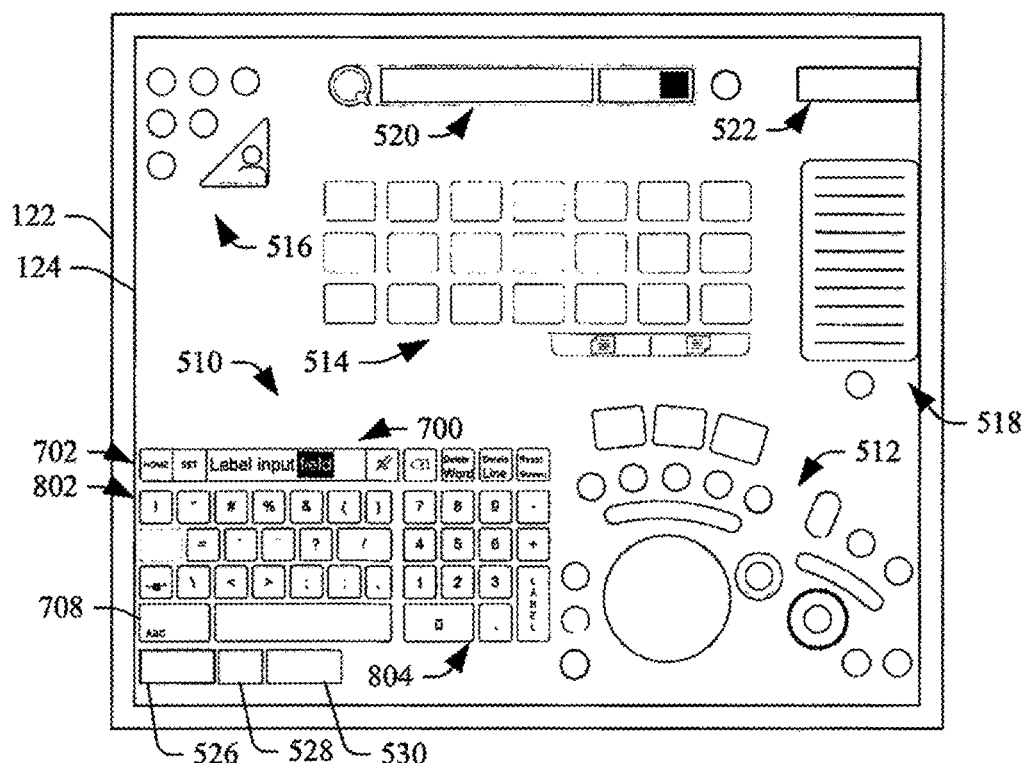
FIG. 8 illustrates another example of an annotation cluster of the touch screen user interface of FIG. 5.

In the illustrated example, the touch screen control 526 invokes the keyboard control layout. The keyboard control layout is task sensitive and changes behavior depending on situation. It can become a search, text field entry, or numerical pad. FIGS. 7 and 8 show examples of keyboard control layouts 700. In FIG. 7, the control layout includes a set of common controls 702 (i.e., shared by both control layouts), alphabetic character and other controls 704 (e.g., letters, upper/lowercase toggle, some punctuation, spacebar, etc.), and reserved controls 706. In FIG. 8, the control layout includes the set of common controls 702, special characters and other controls 802, and numeric controls 804. In FIGS. 7 and 8, a toggle control 708 toggles the layout between that of FIG. 7 and that of FIG. 8.

Figure 9:
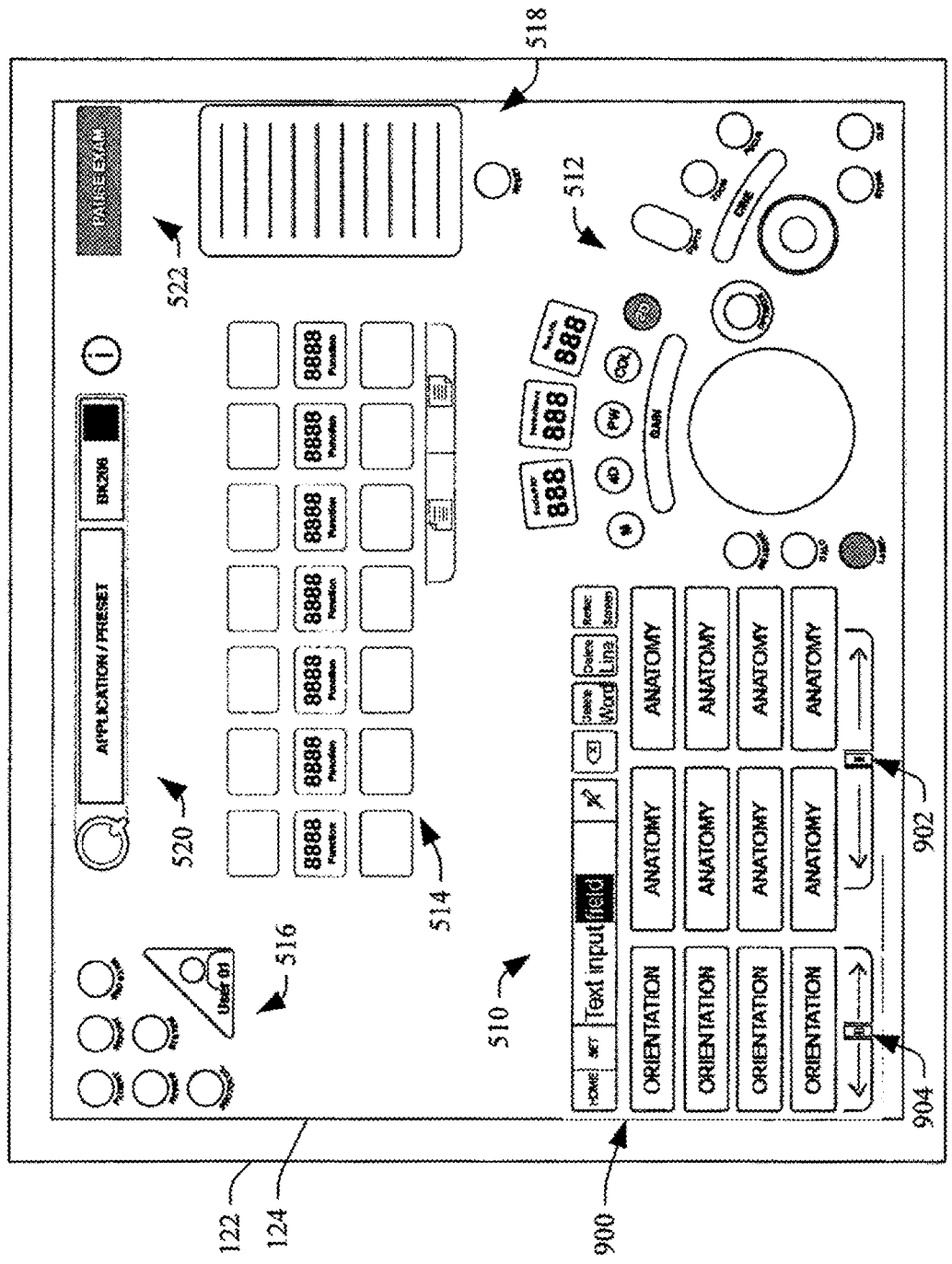
FIG. 9 illustrates an example of a predetermined labels cluster of the touch screen user interface of FIG. 5.

Returning to FIG. 5, in the illustrated example, the touch screen control 528 invokes the predefined labels layout. FIG. 9 shows an example of the predefined labels layout 900. The predefined labels layout provides predetermined labels that are ready to use keywords that can be customized to the user's needs. In this example, the predefined labels layout includes controls 902 for selecting anatomy from a predetermined set of anatomy, and controls 904 for selecting an orientation from a predetermined set of orientations for the selected anatomy.

Figure 10:
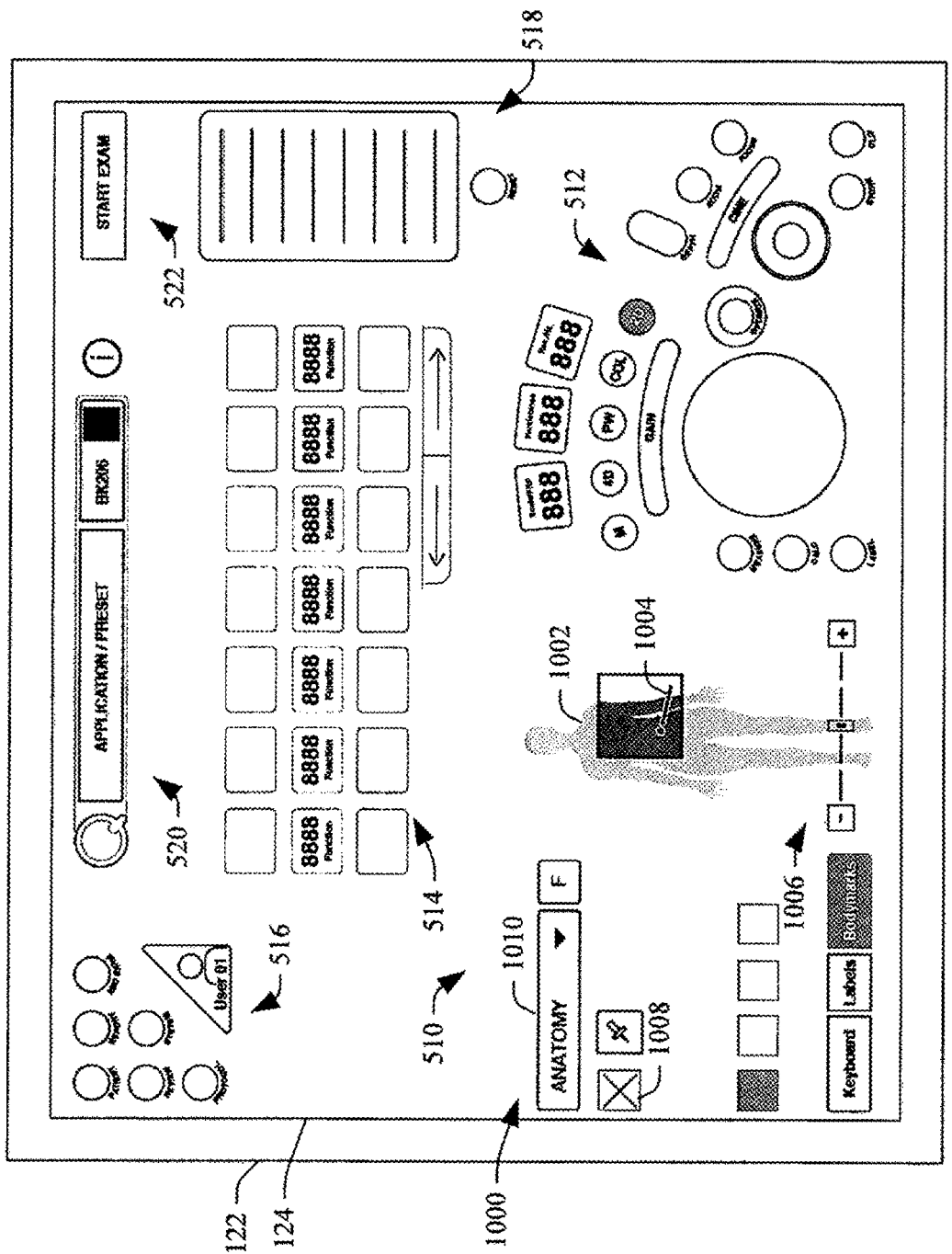
FIG. 10 illustrates an example of a bodymark cluster of the touch screen user interface of FIG. 5.
Figure 11:
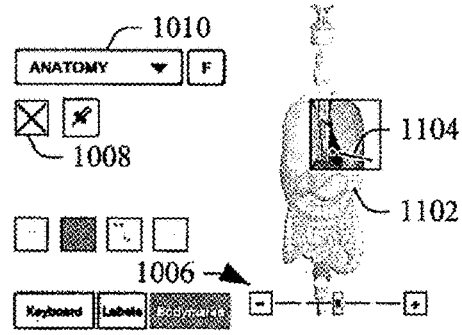
FIG. 11 illustrates an example of the bodymark cluster of FIG. 10 with a graphical representation of an organ.

Returning to FIG. 5, the touch screen control 530 invokes a bodymarker layout 1000, as shown in FIG. 10, which includes a tool to graphically label a graphical representation of a patient with a graphical representation of the transducer array. FIG. 10 shows a profile 1002 of a patient and a graphical representation of the transducer array 1004. FIG. 11 shows a profile 1102 of an organ and a graphical representation of the transducer array 1104. In general, the user can choose from various renderings of the body including external, internal, and any that are anatomy specific, for example, through an anatomy control 1010. Layer views can be selected as button presses and correspond to the rotation and position of the previous view. A magnification control 1006 allows for zooming in and out of the profiles 1002 and 1102.

Figure 12:
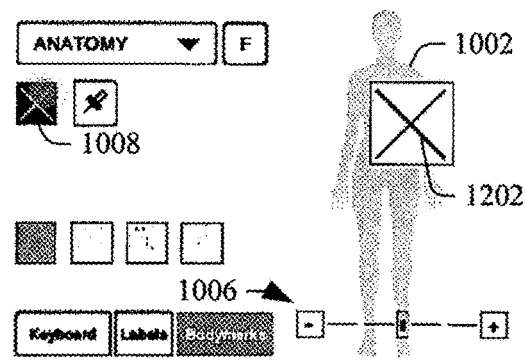
FIG. 12 illustrates an example of the bodymark cluster of FIG. 10 in which the graphical representation of the patient and transducer are not displayed on the display monitor.

The profiles 1002 or 1102 and the graphical representations 1004 and 1104 are mimicked on the display monitor 112. FIGS. 10, 11 and 12 show an example in which the bodymarker layout includes a control 1008 that invokes toggling display of such information on and off from the display monitor 112. In FIG. 10, the control 1008 is activated to display the profile 1002 and the graphical representation of the transducer array 1004 via the display monitor 112. In FIG. 11, the control 1008 is activated to display the profile 1102 and the graphical representation of the transducer array 1104 via the display monitor 112. In FIG. 12, the control 1008 is activated to not display the profile 1002 or the graphical representation 1004 on the display monitor 112. In FIG. 12, this is indicated via indicia 1202 overlaid over the profile 1002 and the graphical representation 1004.

Figure 14:
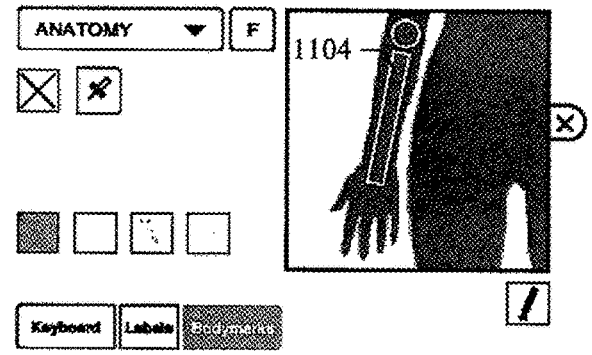
FIG. 14 illustrates an example of the bodymark cluster of FIG. 10 showing a zoomed in view of the graphical representation of the transducer.
Figure 15:
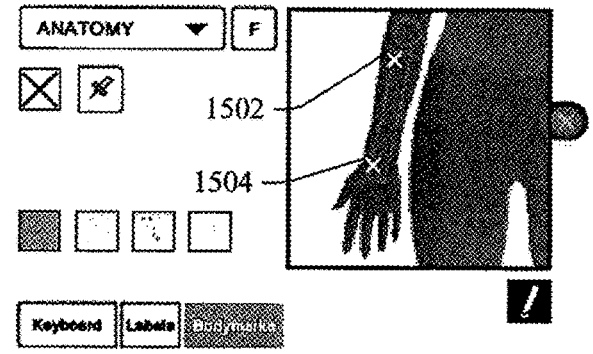
FIG. 15 illustrates an example of the bodymark cluster of FIG. 10 in which points of interest are identified.
Figure 13:
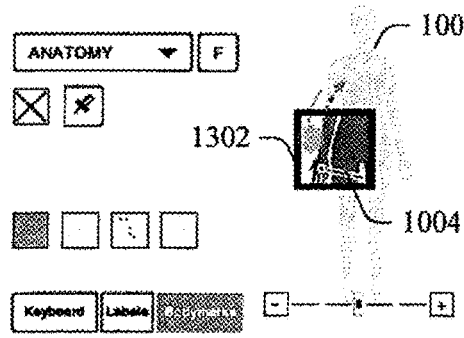
FIG. 13 illustrates an example of the bodymark cluster of FIG. 10 in which the graphical representation of the transducer is moved.
Figure 16:
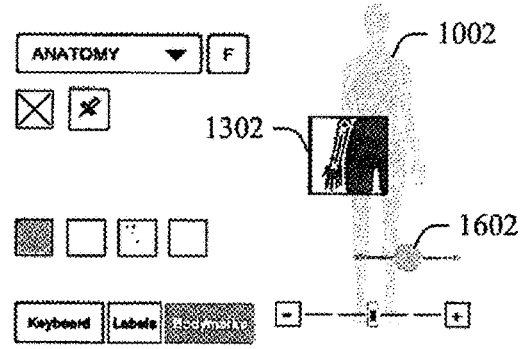
FIG. 16 illustrates an example of the bodymark cluster of FIG. 10 in which the graphical representation of the patient is rotated.

FIG. 13 shows an example in which the graphical representation of the transducer array 1004 of FIG. 10 can be moved through a click and drag on an annotation box 1302 including the graphical representation of the transducer array 1004 and/or other operation. FIG. 14 shows a zoomed in view of the graphical representation of the transducer array 1004 in connection with an arm of the representation of the patient. FIG. 15 shows user placed points of interest 1502 and 1504 in connection with the graphical representation of the transducer array 1004 shown in FIG. 14. In this example, the user simply taps on a location on the graphical representation of the transducer array 1004 to place the point of interest 1502 and/or 1504. FIG. 16 shows an example in which a control 1602 allows for rotating the bodymark view by dragging left/right on the body outside the annotation box.

Figure 17:
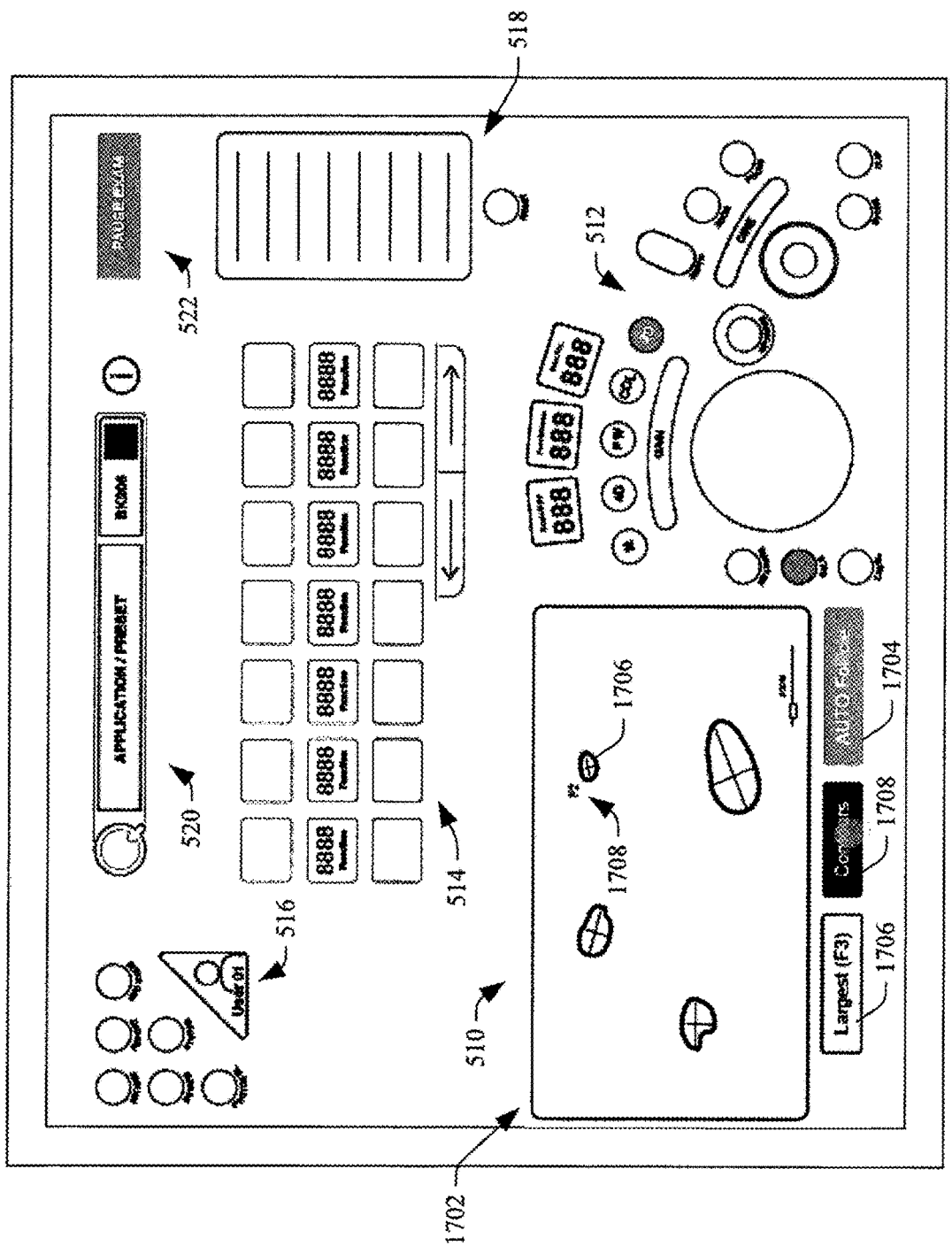
FIG. 17 illustrates an example of a follicle cluster of the touch screen user interface of FIG. 5.
Figure 18:
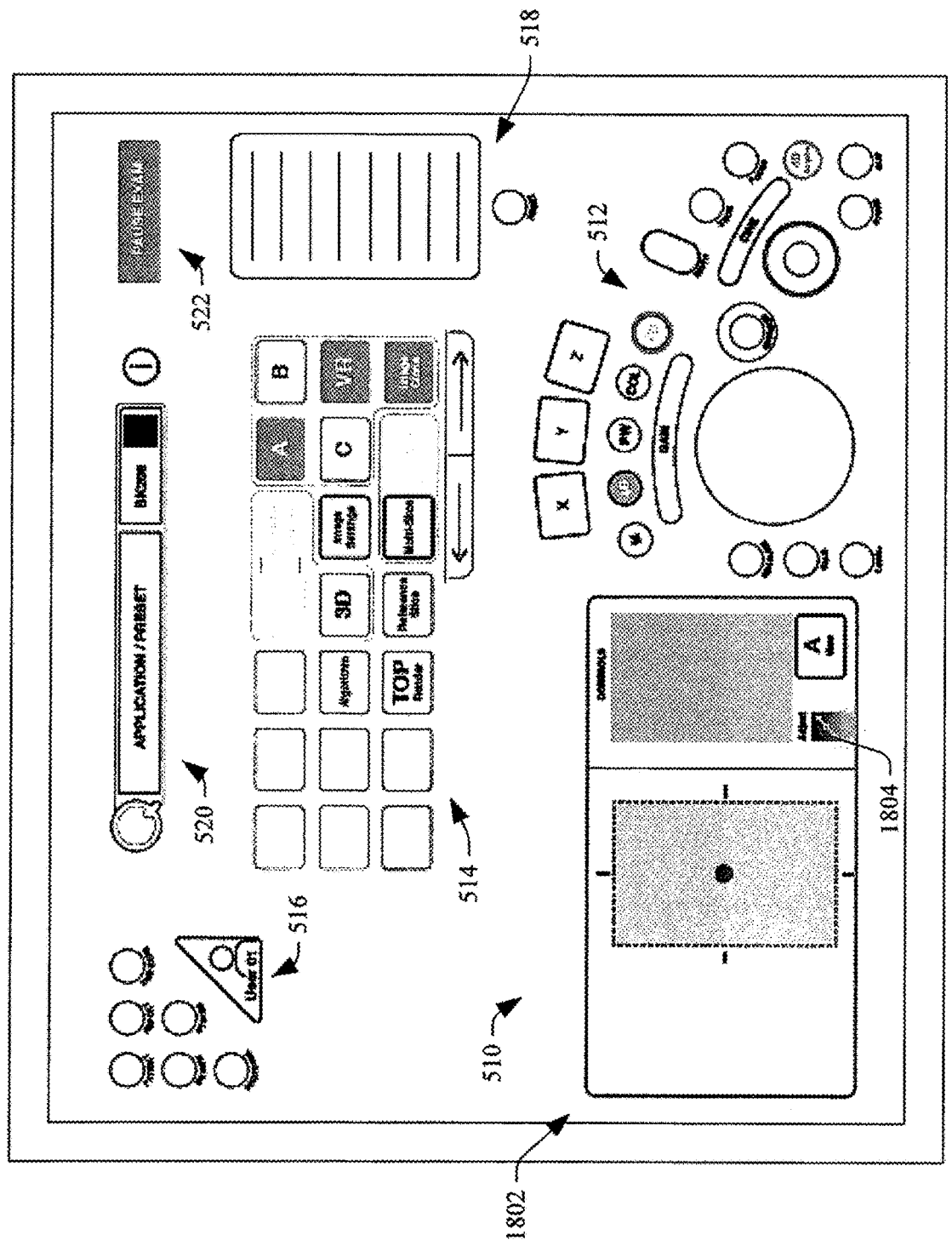
FIG. 18 illustrates an example of a 3D/4D cluster of the touch screen user interface of FIG. 5.

Returning to FIG. 5, the annotation cluster 510 is replaced with a follicle cluster 1702, as shown in FIG. 17, in certain modes of operation (e.g., follicle mode). The follicle cluster 1702 includes a control 1704 that allows a user to activate follicle mode. Actuating a displayed follicle 1706 makes an automatic measurement 1708 of the follicle 1706 which is displayed next to the follicle 1706. A control 1710 acts as a quick link to selecting the largest follicle. A control 1712 allows a user to adjust the contours of the follicle measurement. In another instance, the annotation cluster 510 is replaced with a clone 1802 of the image and an adjust control 1804, as shown in FIG. 18, for example, when in the 3D/4D mode. Activating the adjust control 1804 activates corner brackets, which can be used to modify the area selected. In yet another instance, the annotation cluster 510 is replaced with a calc cluster, which includes controls for selecting anatomy of interest. When a control for particular anatomy is selected, the anatomy cluster is reduced, and left and right orientation controls that correspond to the selected anatomy are visually presented in the cluster.

Figure 19:
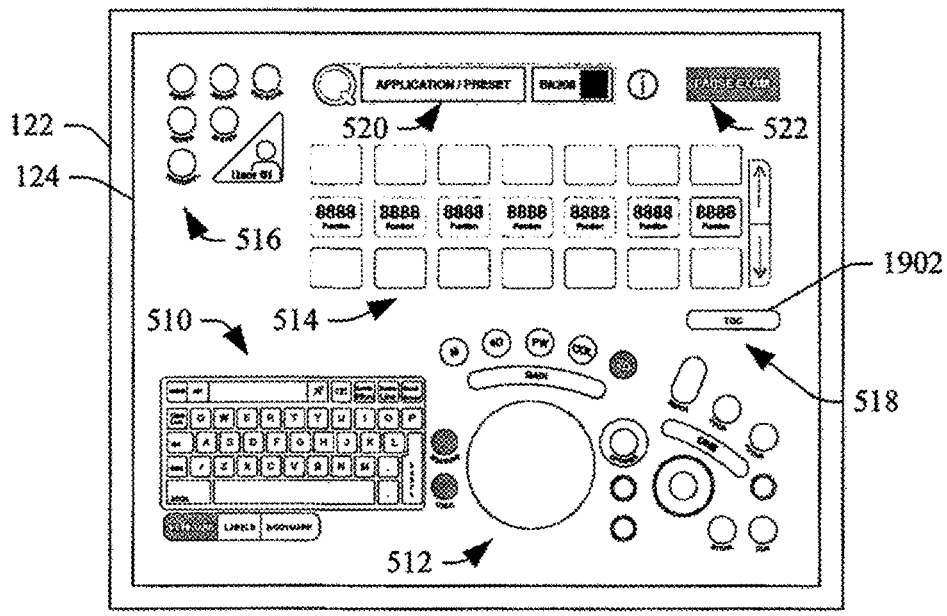
FIG. 19 illustrates a variation of the touch screen user interface of FIG. 5 in which the touch panel area is smaller and in connection with a single TGC cluster control.
Figure 20:
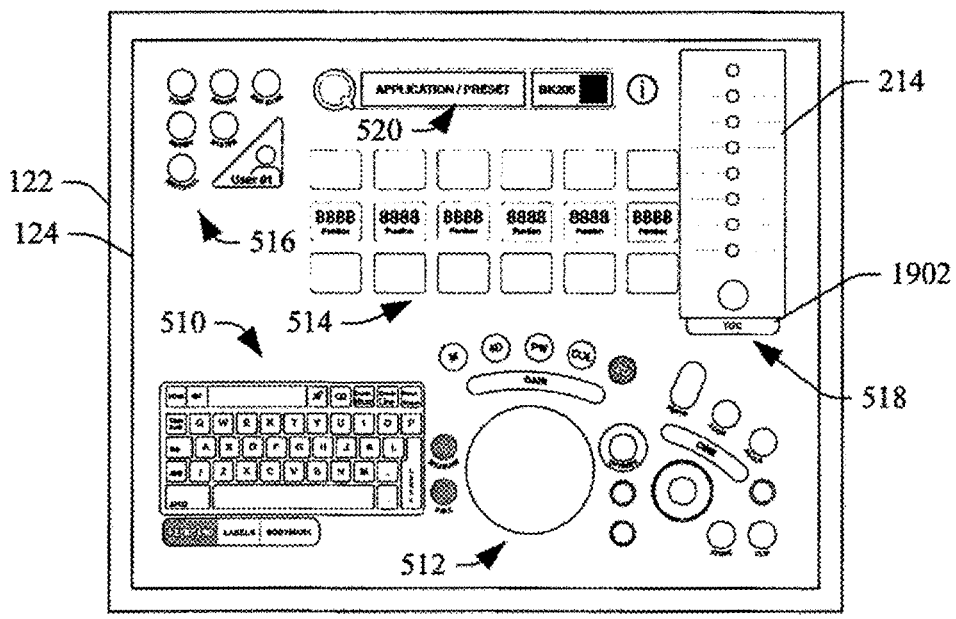
FIG. 20 illustrates a variation of the touch screen user interface of FIG. 5 in which the touch panel area is smaller and in connection with multiple TGC cluster controls.

Turning now to FIGS. 19 and 20, a variation of the configuration of FIG. 5 is illustrated. In this variation, the touch screen panel 124 geometry is smaller, e.g., having a diagonal in a range of 10" to 16", such as 15", 15.5" and/or other size smaller than that discussed on connection with FIG. 5. As such, the clusters 510-522 are spatially closer together relative to the configuration of FIG. 5, with one or more clusters reduced in size (e.g., the annotation cluster 510), one or more clusters reduced in number of visual elements (e.g., the contextual cluster 514), one or more clusters graphically represented using more compact graphical indicia (e.g., the TGC cluster 518), and/or otherwise modified.

In FIG. 19, the TGC cluster 518 is shown with only a single toggle button 1902. In FIG. 20, the TGC cluster 518 is shown with the single toggle button 1902 and the control 214 described in connection with FIGS. 2 and 5. The single toggle button 1902 toggles display of the TGC cluster 510 between only the single toggle button 1902 of FIG. 19 and concurrent display of the single toggle button 1902 and the control 214 of FIG. 20. In FIG. 20, the control 214 partially overlaps the contextual cluster 514 and covers the exam cluster 522. By bringing the control 214 out as such, the touch screen controller 148 brings controls for the currently activated TGC cluster 518 out to the user for access when the user is to use the TGC controls 214. In other embodiments, the control 214 is otherwise rendered, for example, to overlap more, less, and/or other clusters.

Figure 21:
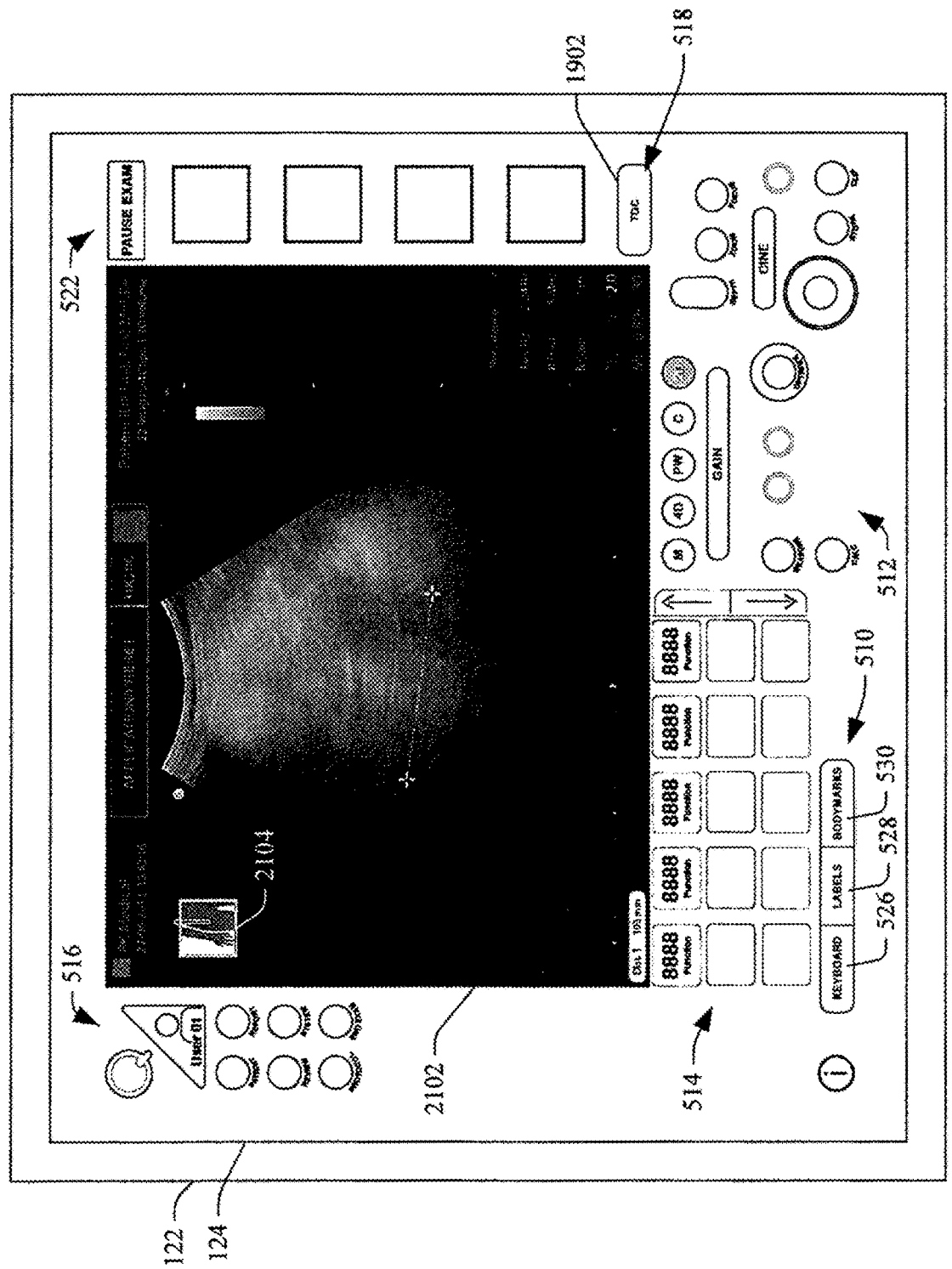
FIG. 21 illustrates a variation of the touch screen user interface of FIG. 5 which includes an image display region and a landscape orientation.

FIG. 21 illustrates another variation in which the touch panel 124 further includes an image display region 2102. The image display region 2102 is integrated with the touch panel 124, includes soft buttons to access application/presets and transducers, and displays the same image displayed by the display monitor 112. Similar to FIGS. 19 and 20, the spatial layout of the clusters 510-522 is modified, however, in FIG. 21 to accommodate the image display region 2102. For example, the TGC cluster 518, similar to FIGS. 19 and 20, is graphically represented using the single toggle button 1902. Likewise, the annotation cluster 510 is represented using a reduced number of controls. In this example, only the controls 526, 528, and 530 (and not the region 524) are graphically displayed. In the example of FIG. 21, the graphical representation of the patient profile 1002 and the graphical representation of the transducer array 1004 are shown in the image display region 2102 at 2104.

Figure 22:
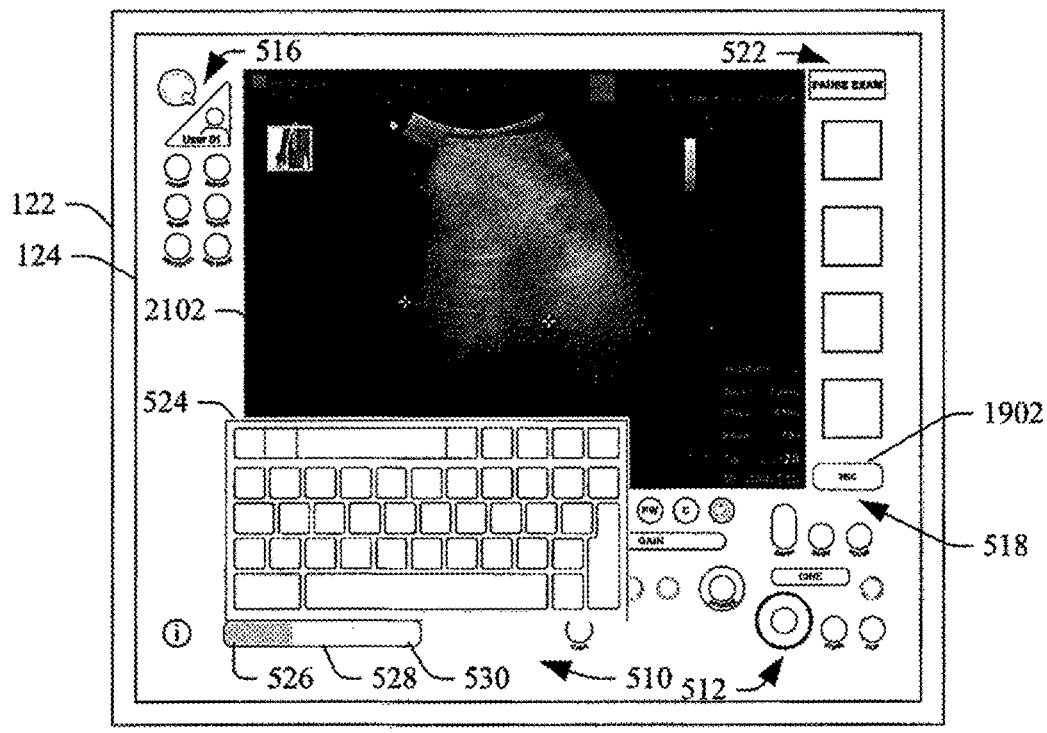
FIG. 22 illustrate the variation of FIG. 21 in connection with the annotation cluster.

FIG. 22 shows the touch panel 124 of FIG. 21 with the control 526 of the annotation cluster 510 activated. As shown, when activated, the region 524 is also displayed with the keyboard layout of FIG. 7. In this example, the region 524 partially overlaps the contextual cluster 514 and the image display region 2102. By bringing the region 524 out as such, the touch screen controller 148 brings controls for the currently activated annotation cluster 510 out to the user for access. In other embodiments, the region 524 is otherwise rendered, for example, to overlap more, less, and/or other clusters, including in a region of the touch panel 124 in which the region 524 and the controls 526-530 are separated by other clusters.

Figure 23:
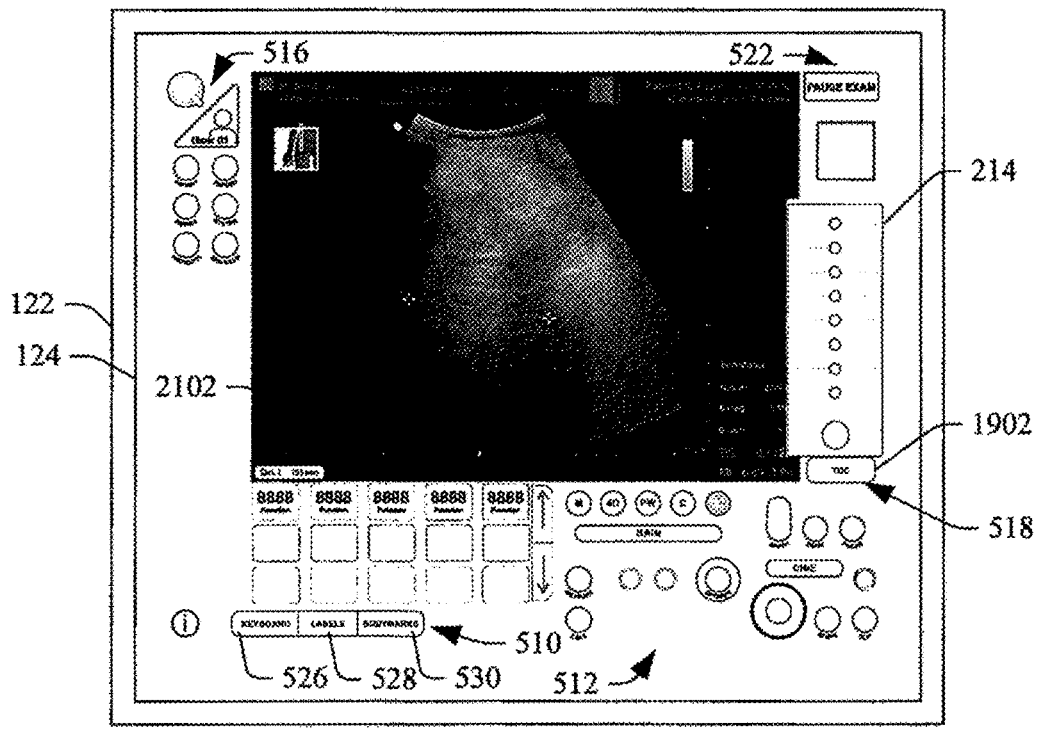
FIG. 23 illustrate the variation of FIG. 21 in connection with the TGC cluster.

FIG. 23 shows the touch panel 124 of FIG. 21 with the single toggle button 1902 activated to display the control 214. In this example, the control 214 partially overlaps the image display region 2102. By bringing the control 214 out as such, the touch screen controller 148 brings controls for a currently activated cluster out to the user for access. In other embodiments, the control 214 is otherwise rendered, for example, to overlap more, less, and/or other clusters, including in a region of the touch panel 124 in which the control 214 and the single toggle button 1902 and the control 214 are separated by other clusters.

Figure 24:
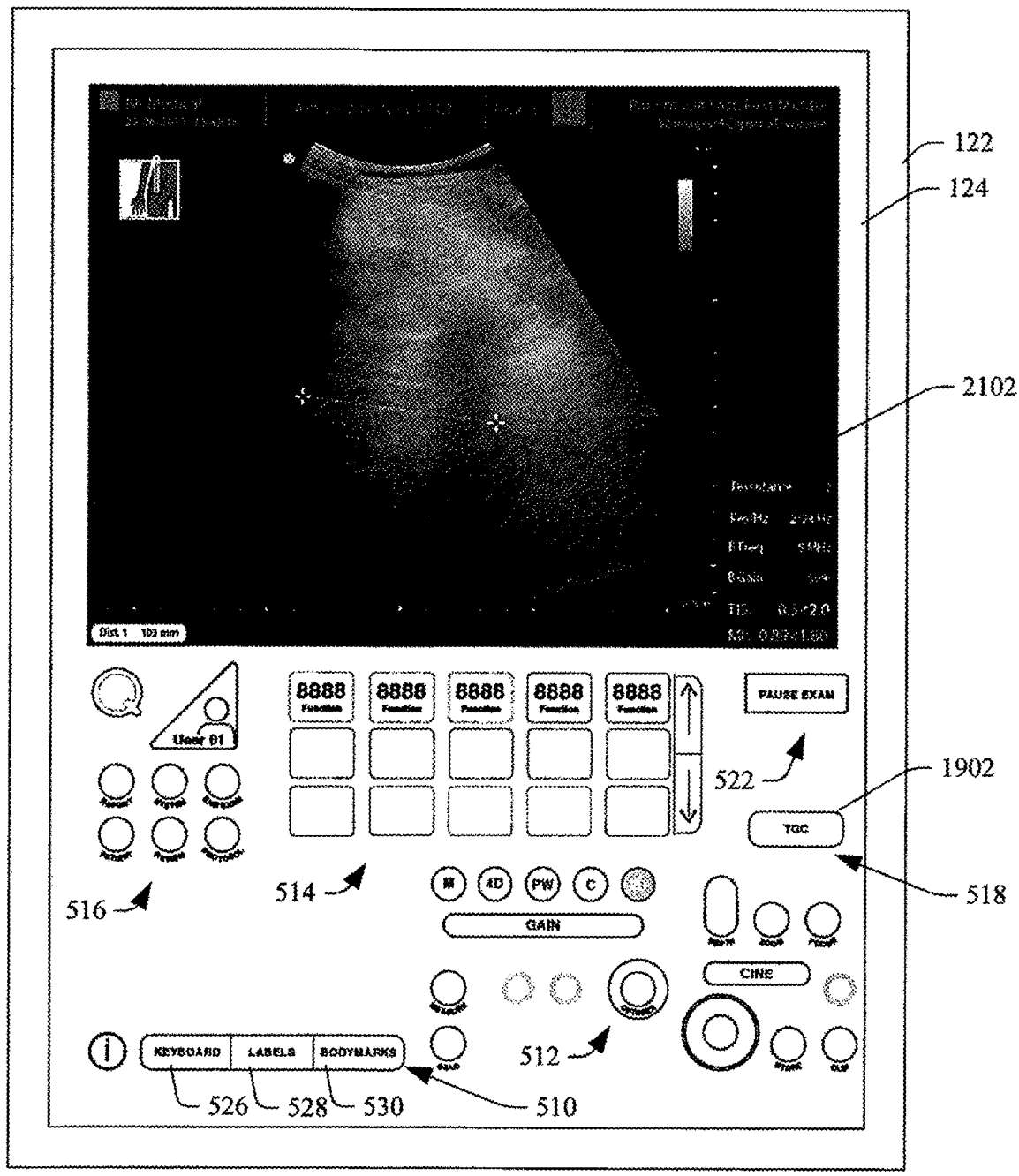
FIG. 24 illustrates a variation of the touch screen user interface of FIG. 5 which includes an image display region and a portrait orientation.

FIG. 21 shows a landscape display configuration. FIG. 24 shows a variation of FIG. 21 with a portrait display configuration. Likewise, the spatial layout of the clusters 510-522 is modified to accommodate the image display region 2102. For example, the TGC cluster 518 is graphically represented using the single toggle button 1902 and the annotation cluster 510 is represented with only the controls 526, 528, and 530 (and not the region 524). FIG. 25 shows the touch panel 124 of FIG. 24 with the control 526 of the annotation cluster 510 activated, which causes display of the region 524. In this example, the region 524 partially overlaps the primary cluster 512, the contextual cluster 514 and the pre/post cluster 516 and the image display region 2102.

FIG. 26 shows the touch panel 124 of FIG. 24 with the single toggle button 1902 of the TGC cluster 510 activated, which causes display of the control 214. In this example, the control 214 partially overlaps the image display region 2102 and the exam cluster 522. Likewise, with FIGS. 25 and 26, bringing the region 524 and the control 214 out as such brings controls for a currently activated cluster out to the user for access. Furthermore, in other embodiments, the region 524 and/or the control 214 are otherwise rendered, as described herein and/or otherwise.

Figure 28:
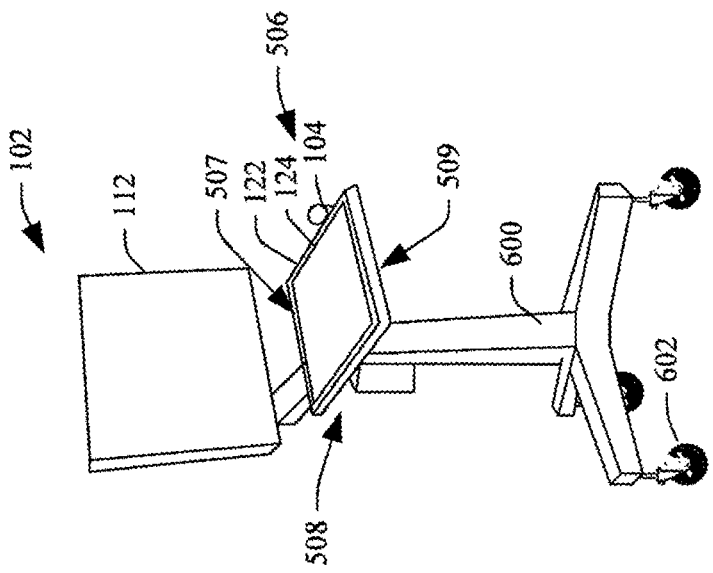
FIGS. 27 and 28 illustrate an ultrasound imaging system with a rotatable touch screen user interface.
Figure 27:
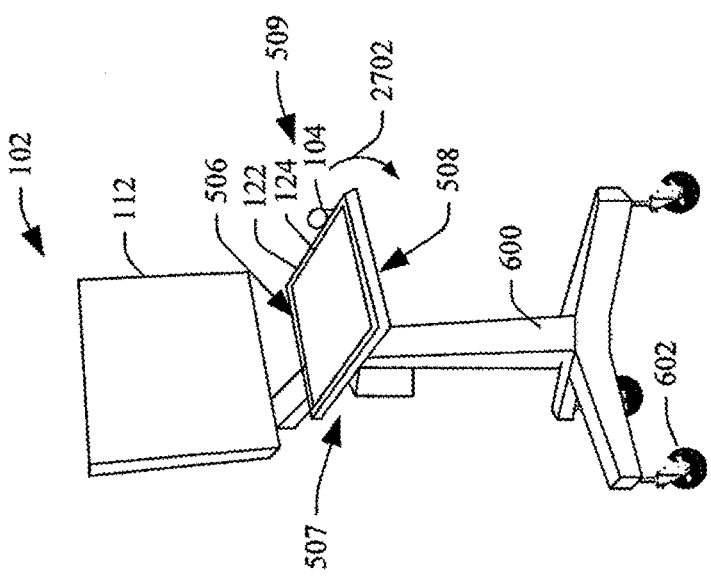

As discussed herein, the touch screen user interface 122 of FIG. 5 is larger than that of the touch screen user interface 122 of FIG. 19. It is to be appreciated that one or both of the touch screen user interfaces 122 of FIGS. 5 and 19 may be configured to not visually display the image display region 2102, display the image display region 2102, or to be able to alternatively display the image display region 2102 or not display the image display region 2102, for example, through activation of a corresponding toggle button and/or otherwise. In another instance, one or both of the touch screen user interfaces 122 of FIGS. 5 and 19 can be physically rotated to switch between the landscape display configuration of FIG. 21 and the portrait display configuration of FIG. 24. FIGS. 27 and 28 illustrate example clockwise rotation 2702 of ninety-degrees (90°).

The examples shown in FIGS. 21-26 include the image display region 2102 on the touch panel 124. This configuration of the touch panel 124 can be utilized with the ultrasound imaging system 102 and/or an ultrasound imaging system without a separate display monitor, such as the ultrasound imaging system 102 without the display monitor 112.

In FIG. 27, the sides 506, 507, 508 and 509 are as described in connection with FIGS. 5 and 6 with the side 506 proximate to the display monitor 112, the side 508 distal to the display monitor 112, and the sides 507 and 509 extending there between. In FIG. 28, the sides 506 and 508, after rotating, now both extend equally between the display monitor 112, the side 507 is at the backside, and the side 509 is at the front side of the imaging system, or where the user would stand to operate the touch panel 124. The touch screen controller 148 rotates the display of the information display in the touch panel 124 so as to maintain the special orientation of the information display in the touch panel 124 with respect to the display monitor 112. In another example, the touch screen user interfaces 122 is configured to additionally or alternative counter-clockwise. Furthermore, such rotation may be limited to 90° or be greater than 90°, for example, 135°, 270°, 360°, etc.

In one embodiment, the ultrasound system is an interventional ultrasound system used to guide a urological, surgical, anesthesia, or other intervention to a desired treatment location in the interior anatomy of the patient. Treatments may be provided through a needle used for drug delivery or for obtaining a biopsy or other tissue samples, RF or other ablation, or the like. Such interventions are often provided in a sterile environment, or otherwise require disinfection or other cleaning of the touch panel 124 between procedures. As will be appreciated, and as described above, aspects of the present invention facilitate such cleaning while providing the operator with a convenient user interface. The touch screen interface 122 the touch panel 124 can be utilized with a sterile or non-sterile plastic, latex, cloth, drape, etc. placed over the touch panel 124, by a user wearing sterile gloves, a combination thereof, etc.

Furthermore, the touch panel 124 is readily cleanable. This includes the recessed controls of the primary cluster 512 and/or other cluster, as well as the other regions of the touch panel 124, which include many soft controls and lack crevices such as those around keys of a mechanical keyboard, trackball, etc. The touch panel 124 may also be used in connection with a general purpose ultrasound systems such as those commonly used in ob/gyn, cardiology, general imaging or the like.

Although the touch panel 124 has been described herein in connection with the ultrasound imaging system 102, in another embodiment the touch panel 124 is utilized with a computer tomography, magnetic resonance, x-ray and/or other imaging modality. The controls and clusters in such an embodiment would correspond to the particular imaging modality.

Figure 29:
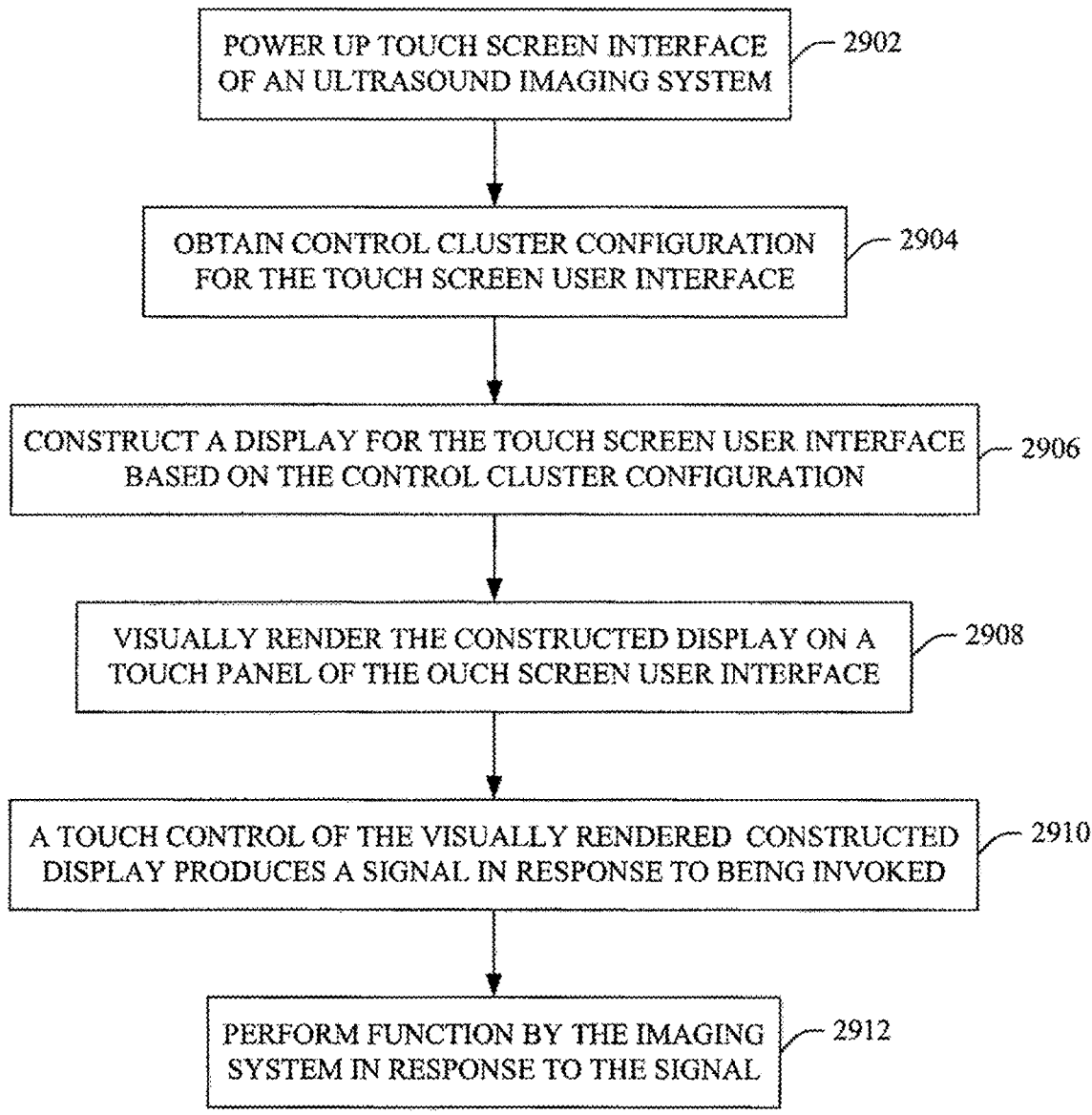
FIG. 29 illustrates example method in accordance with the description herein.

FIG. 29 illustrates example method in accordance with one or more of the embodiments described herein.

It is to be appreciated that the ordering of the below acts is for explanatory purposes and not limiting. As such, other orderings are also contemplated herein. In addition, one or more of the acts may be omitted and/or one or more other acts may be included.

At 2902, a touch screen user interface 122 of an ultrasound imaging system 102 is powered on.

At 2904, a control cluster configuration for the touch screen user interface 122 is obtained.

At 2906, a display is constructed by the touch screen controller 148 for the touch screen user interface based on the control cluster configuration.

At 2908, the constructed display is visually rendered by the touch screen controller 148 on the touch panel 124 of the touch screen user interface 122.

At 2910, a touch control of the visually rendered display produces a signal in response to actuation of the touch control by a user of the system 102.

At 2912, the imaging system 102 performs an ultrasound imaging function in response to the signal.

At least a portion of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system comprising:
a touch screen user interface with a touch panel, wherein the touch panel includes a plurality of different clusters of controls including a first cluster in a first sub-region and with a tactile control, wherein the tactile control includes at least one of: a rough surface, a recess or an indentation, and one or more other clusters in one or more other different sub-regions and with soft controls, and wherein the tactile control includes a structural surface feature that corresponds to an ultrasound operation of one of the different groupings of ultrasound imaging operations controlled by the tactile control, wherein the tactile control provides haptic feedback; and
a touch screen controller that visually renders the one or more other clusters in the one or more other different sub-regions spatially arranged with respect to each other based on a predetermined control cluster configuration for the touch screen user interface, wherein the one or more other clusters include controls that correspond to different groupings of ultrasound imaging operations of the ultrasound imaging system.

2. The ultrasound imaging system of claim 1, further comprising:
a display,
wherein the touch screen user interface further includes:
a back side;
a front side, wherein the back side and the front side are opposing sides of the touch screen user interface, the back side is a first distance from the display, the front side is a second distance from the display, and the second distance is greater than the first distance; and
a region between the back side and the front side, the region including:
a back side sub-region next to the back side; and
a front side sub-region located between the back side sub-region and the front side, and
wherein the first cluster is disposed in the front side sub-region and includes primary controls to control an imaging operation of one of the different groupings of ultrasound imaging operations, and an annotation cluster of the one or more other clusters includes controls that allow input of information to annotate information acquired in an examination of a patient.

3. The ultrasound imaging system of claim 2, wherein the annotation cluster is disposed in the front side sub-region and includes letter keys to enter letters, label keys to indicate anatomical labels, and marker keys to add markers.

4. The ultrasound imaging system of claim 3, wherein at least two of the letter keys, the label keys, and the marker key are displayed alternately in a same place.

5. The ultrasound imaging system of claim 2, further including a contextual cluster that includes dynamic controls that provide functionality corresponding to an active control of another cluster.

6. The ultrasound imaging system of claim 5, wherein the contextual cluster is disposed in the back side sub-region.

7. The ultrasound imaging system of claim 5, wherein the one or more other clusters further include one or more of a pre/post cluster, a time-gain control (TGC) cluster, an application cluster, and an exam cluster.

8. The ultrasound imaging system of claim 7, wherein the pre/post cluster includes controls that are accessed before and/or after an imaging examination.

9. The ultrasound imaging system of claim 7, wherein the time-gain control (TGC) cluster includes controls to control amplification of received ultrasound signals as a function of time.

10. The ultrasound imaging system of claim 7, wherein the application cluster includes controls to access one or more of applications, presets, transducers, or quick start information.

11. The ultrasound imaging system of claim 7, wherein the exam cluster includes controls to control one or more of start, pause, resume, or add an exam.

12. The ultrasound imaging system of claim 7, wherein the annotation cluster is located in the front side sub-region, and wherein the contextual cluster, the pre/post cluster, the time-gain control (TGC) cluster, the application cluster and the exam cluster are located in the back side sub-region.

13. The ultrasound imaging system of claim 12, wherein locations of the contextual cluster, the pre/post cluster, the time-gain control (TGC) cluster, the application cluster and the exam cluster do not visibly obscure or hinder access to the primary controls or the annotation controls.

14. The ultrasound imaging system of claim 1, wherein the tactile control is stationarily positioned at a fixed, non-moveable location in the first sub-region.

15. The ultrasound imaging system claim 1, wherein the structural surface feature identifies an imaging operation of one of the different groupings of the ultrasound operation to a user touching the structural surface feature.

16. The ultrasound imaging system of claim 1, wherein the first cluster includes a first control configured to activate a 2D mode, a second control configured to activate a 3D mode, a third control configured to activate a color Doppler mode, a fourth control configured to activate a pulse wave Doppler mode, a fifth control configured to activate a 4D mode, and a sixth control configured to activate a motion mode.

17. The ultrasound imaging system of claim 16, wherein the first cluster further includes a seventh control configured to control a depth, an eighth control configured to control a gain, a ninth control configured to control a zoom, and a tenth control configured to control a focus.

18. The ultrasound imaging system of claim 1, wherein the one or more other clusters are positionable at different locations on the touch panel.

19. The ultrasound imaging system of claim 1, wherein the soft controls of each of the one or more other clusters is variable.

20. The ultrasound imaging system of claim 1, wherein the touch panel includes a back side and a front side.

21. The ultrasound imaging system of claim 20, wherein a second cluster of the one or more other clusters is closer to the front side than the back side.

22. The ultrasound imaging system of claim 20, wherein a third cluster of the one or more other clusters is closer to the back side than the front side.

23. The ultrasound imaging system of claim 20, further comprising
a display monitor disposed at the back side.

24. The ultrasound imaging system of claim 1, wherein the touch panel includes an image display region, and the ultrasound imaging system does not include a display monitor.

25. The ultrasound imaging system of claim 1, wherein a second cluster of the one or more other clusters includes a first set of controls and a control display region, and a different second set of sub-controls is rendered in the control display region depending on which control of the first set of controls is active.

26. The ultrasound imaging system of claim 25, wherein the control display region is visually displayed only when a control of the first set of controls is active.

27. The ultrasound imaging system of claim 25, wherein the touch screen controller changes which of the different second set of sub-controls is visually displayed in the control display region in response to receiving a signal indicating a change in an active control of the first set of controls.

28. The ultrasound imaging system of claim 25, wherein the first set of controls corresponds to annotation controls configured to add information to a visually displayed image.

29. The ultrasound imaging system of claim 25, wherein the first set of controls corresponds to keyboard controls configured to enter information.

30. The ultrasound imaging system of claim 25, wherein the first set of controls corresponds to bodymarker controls configured to identify a location of a transducer array on a graphical representation of a subject.

31. The ultrasound imaging system of claim 30, wherein the bodymarker controls include a display control configured to toggle display of the graphical representation on or off.

32. The ultrasound imaging system of claim 30, wherein the bodymarker controls includes an anatomy control that toggles display of the graphical representation through different external and internal anatomical representations of a patient.

33. The ultrasound imaging system of claim 30, wherein the bodymarker controls includes a rotate control to rotate the graphical representation in the touch panel, a magnify control configured to magnify the graphical representation in the touch panel, or the rotate control and the magnify control.

34. An ultrasound imaging system comprising:
a touch screen user interface with a touch panel, wherein the touch panel includes a plurality of different clusters of controls including a first cluster in a first sub-region and with a tactile control, wherein the tactile control include at least one of: a rough surface, a recess or an indentation, and one or more other clusters in one or more other different sub-regions and with soft controls, wherein the tactile control includes a structural surface feature that identifies an imaging operation to a user touching the structural surface feature, wherein the tactile control provides haptic feedback; and
a touch screen controller that visually renders the one or more other clusters in the one or more other different sub-regions spatially arranged with respect to each other based on a predetermined control cluster configuration for the touch screen user interface, wherein the one or more other clusters include controls that correspond to different groupings of ultrasound imaging operations of the ultrasound imaging system.

35. The ultrasound imaging system of claim 34, further comprising:
a display,
wherein the touch screen user interface further includes:
a back side;
a front side, wherein the back side and the front side are opposing sides of the touch screen user interface, the back side is a first distance from the display, the front side is a second distance from the display, and the second distance is greater than the first distance; and
a region between the back side and the front side, the region including:
a back side sub-region next to the back side; and
a front side sub-region located between the back side sub-region and the front side, and
wherein the first cluster is disposed in the front side sub-region and includes primary controls to control an imaging operation of one of the different groupings of ultrasound imaging operations, and an annotation cluster of the one or more other clusters includes controls that allow input of information to annotate information acquired in an examination of a patient.

36. The ultrasound imaging system of claim 35, wherein the annotation cluster is disposed in the front side sub-region and includes letter keys to enter letters, label keys to indicate anatomical labels, and marker keys to add markers.

37. The ultrasound imaging system of claim 36, wherein at least two of the letter keys, the label keys, and the marker key are displayed alternately in a same place.

38. The ultrasound imaging system of claim 35, further including a contextual cluster that includes dynamic controls that provide functionality corresponding to an active control of another cluster.

39. The ultrasound imaging system of claim 38, wherein the contextual cluster is disposed in the back side sub-region.

40. The ultrasound imaging system of claim 38, wherein the one or more other clusters further include one or more of a pre/post cluster, a time-gain control (TGC) cluster, an application cluster, and an exam cluster.

41. The ultrasound imaging system of claim 40, wherein the pre/post cluster includes controls that are accessed before, after or before and after an imaging examination.

42. The ultrasound imaging system of claim 40, wherein the time-gain control (TGC) cluster includes controls to control amplification of received ultrasound signals as a function of time.

43. The ultrasound imaging system of claim 40, wherein the application cluster includes controls to access one or more of applications, presets, transducers, or quick start information.

44. An ultrasound imaging system comprising:
a touch screen user interface with a touch panel, wherein the touch panel includes a plurality of different clusters of controls including a first cluster in a first sub-region and with a first tactile control, wherein the first tactile control includes a first rough surface with a first roughness, and one or more other clusters in one or more other different sub-regions and with soft controls, wherein the first tactile control provides haptic feedback; and
a touch screen controller that visually renders the one or more other clusters in the one or more other different sub-regions spatially arranged with respect to each other based on a predetermined control cluster configuration for the touch screen user interface, wherein the one or more other clusters include controls that correspond to different groupings of ultrasound imaging operations of the ultrasound imaging system.

45. The ultrasound imaging system of claim 44, wherein the touch panel includes a second first tactile control with a second rough surface with a second roughness.

46. The ultrasound imaging system of claim 45, wherein the first roughness and the second roughness are a different roughness.

47. The ultrasound imaging system of claim 46, wherein the first roughness corresponds to a first ultrasound operation of one of the different groupings of ultrasound imaging operations controlled by the first tactile control and the second roughness corresponds to a second different ultrasound operation of one of the different groupings of ultrasound imaging operations controlled by the second tactile control.

* * * * *